United States Patent
Maehara

(10) Patent No.: US 11,584,909 B2
(45) Date of Patent: Feb. 21, 2023

(54) CELL POTENTIAL DETECTION DEVICE, METHOD OF MANUFACTURING CELL POTENTIAL DETECTION DEVICE, AND INFORMATION PROCESSING SYSTEM

(71) Applicant: SONY SEMICONDUCTOR SOLUTIONS CORPORATION, Kanagawa (JP)

(72) Inventor: Masataka Maehara, Tokyo (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 357 days.

(21) Appl. No.: 16/651,392

(22) PCT Filed: Sep. 21, 2018

(86) PCT No.: PCT/JP2018/034978
§ 371 (c)(1),
(2) Date: Mar. 27, 2020

(87) PCT Pub. No.: WO2019/069708
PCT Pub. Date: Apr. 11, 2019

(65) Prior Publication Data
US 2020/0283717 A1    Sep. 10, 2020

(30) Foreign Application Priority Data

Oct. 5, 2017    (JP) .............................. JP2017-195063

(51) Int. Cl.
*G01N 33/487*     (2006.01)
*C12M 1/42*       (2006.01)
(Continued)

(52) U.S. Cl.
CPC ............ *C12M 35/02* (2013.01); *C12M 37/04* (2013.01); *C12M 41/46* (2013.01); *G01N 27/301* (2013.01);
(Continued)

(58) Field of Classification Search
CPC ........................ G01N 27/301; G01N 33/48728
See application file for complete search history.

(56) References Cited

U.S. PATENT DOCUMENTS

| 4,988,302 A | 1/1991 | Smith et al. |
| RE37,977 E | 2/2003 | Sugihara et al. |

(Continued)

FOREIGN PATENT DOCUMENTS

| CN | 1284166 A | 2/2001 |
| EP | 0401660 A1 | 12/1990 |

(Continued)

OTHER PUBLICATIONS

International Search Report and Written Opinion of PCT Application No. PCT/JP2018/034978, dated Dec. 18, 2018, 10 pages of ISRWO.

(Continued)

*Primary Examiner* — Alexander S Noguerola
(74) *Attorney, Agent, or Firm* — Chip Law Group

(57) ABSTRACT

The present disclosure relates to a cell potential detection device, a method of manufacturing the cell potential detection device, and an information processing system that enable prevention of culture solution for a cell from leaking. The cell potential detection device includes: a cell potential detection chip including an electrode unit that detects potential of a cell; a substrate on which the cell potential detection chip is implemented; a first member sealing a connection electrically connecting the cell potential detection chip and the substrate; and a second member layered on the first (Continued)

member, the second member forming a liquid-storage portion that stores culture solution for the cell, together with the first member. The present technology can be applied to, for example, a semiconductor module in which packaged is a chip that detects the potential at an action-potential source point due to a chemical change of a cell.

17 Claims, 22 Drawing Sheets

(51) Int. Cl.
  *C12M 1/12* (2006.01)
  *C12M 1/34* (2006.01)
  *G01N 27/30* (2006.01)
  *G01N 27/416* (2006.01)

(52) U.S. Cl.
  CPC ..... *G01N 27/416* (2013.01); *G01N 33/48728* (2013.01)

(56) References Cited

U.S. PATENT DOCUMENTS

| | | | | |
|---|---|---|---|---|
| 2003/0113833 | A1* | 6/2003 | Oka | G01N 33/48728 436/63 |
| 2005/0279634 | A1* | 12/2005 | Ozaki | G01N 33/48728 204/556 |
| 2006/0096862 | A1* | 5/2006 | Benton | G01N 27/283 204/431 |
| 2014/0220422 | A1* | 8/2014 | Rogers | H05K 1/0283 438/117 |
| 2014/0339102 | A1* | 11/2014 | Urisu | G01N 33/48728 205/794.5 |
| 2017/0074821 | A1* | 3/2017 | Ushio | G01N 27/416 |

FOREIGN PATENT DOCUMENTS

| | | | | |
|---|---|---|---|---|
| EP | | 1040345 | A1 | 10/2000 |
| JP | | 60-244282 | A | 12/1985 |
| JP | | 03-030664 | A | 2/1991 |
| JP | | 08-062209 | B2 | 3/1996 |
| JP | | 11-187865 | A | 7/1999 |
| JP | | 2012-060957 | A | 3/2012 |
| JP | | 2016-182091 | A | 10/2016 |
| KR | | 10-0433913 | A | 6/2004 |
| WO | | 99/034202 | A1 | 7/1999 |
| WO | WO | 9934202 | A1 * | 7/1999 .......... G01N 27/403 |
| WO | | 2007/123035 | A1 | 11/2007 |

OTHER PUBLICATIONS

"Material properties of plastic", Kisei Rubber Co. Ltd., Dec. 7, 2018, 1 page.

* cited by examiner

CELL POTENTIAL DETECTION DEVICE, METHOD OF MANUFACTURING CELL POTENTIAL DETECTION DEVICE, AND INFORMATION PROCESSING SYSTEM

CROSS REFERENCE TO RELATED APPLICATIONS

This application is a U.S. National Phase of International Patent Application No. PCT/JP2018/034978 filed on Sep. 21, 2018, which claims priority benefit of Japanese Patent Application No. JP 2017-195063 filed in the Japan Patent Office on Oct. 5, 2017. Each of the above-referenced applications is hereby incorporated herein by reference in its entirety.

TECHNICAL FIELD

A technology according to the present disclosure (hereinafter, referred to as the present technology) relates to a cell potential detection device, a method of manufacturing the cell potential detection device, and an information processing system, and particularly relates to a cell potential detection device that detects the potential of a cell, a method of manufacturing the cell potential detection device, and an information processing system.

BACKGROUND ART

Until now, it has been proposed that, with an integrated cell setting device including an integrated composite electrode including a plurality of microelectrodes and the lead patterns thereof provided on a glass plate, a cylindrical polystyrene frame having been centered on the center portion of the plurality of microelectrodes is secured to the glass plate and then the polystyrene frame is filled with culture solution (refer to Patent Document 1).

CITATION LIST

Patent Document

Patent Document 1: Japanese Patent Application Laid-Open No. H8-62209

SUMMARY OF THE INVENTION

Problems to be Solved by the Invention

However, in the invention in Patent Document 1, no measure has been considered against leakage of the culture solution with which the polystyrene frame is filled.

The present technology has been made in consideration of such a situation, and an object of the present technology is to enable prevention of culture solution for a cell from leaking.

Solutions to Problems

A cell potential detection device according to one aspect of the present technology, includes: a cell potential detection chip including an electrode unit that detects potential of a cell; a substrate on which the cell potential detection chip is implemented; a first member sealing a connection electrically connecting the cell potential detection chip and the substrate; and a second member layered on the first member, the second member forming a liquid-storage portion that stores culture solution for the cell, together with the first member.

A method of manufacturing a cell potential detection device according to a second aspect of the present technology, includes: a first process of sealing, with a first member, a connection electrically connecting a cell potential detection chip including an electrode unit that detects potential of a cell and a substrate on which the cell potential detection chip is implemented; and a second process of layering a second member on the first member such that the second member forms a liquid-storage portion that stores culture solution for the cell, together with the first member.

An information processing system according to a third aspect of the present technology, includes: a cell potential detection unit configured to detect potential of a cell; and an information processing unit configured to process a detection signal of the potential of the cell, in which the cell potential detection unit includes: a cell potential detection chip including an electrode unit that detects the potential of the cell, the cell potential detection chip being configured to output the detection signal; a substrate on which the cell potential detection chip is implemented; a first member sealing a connection electrically connecting the cell potential detection chip and the substrate; and a second member layered on the first member, the second member forming a liquid-storage portion that stores culture solution for the cell, together with the first member.

According to the first aspect or third aspect of the present technology, the connection electrically connecting the cell potential detection chip and the substrate is sealed, and the liquid-storage portion that stores the culture solution for the cell is formed.

According to the second aspect of the present technology, the first member seals the connection electrically connecting the cell potential detection chip including the electrode unit that detects the potential of the cell and the substrate on which the cell potential detection chip is implemented, and the second member is layered on the first member such that the second member forms the liquid-storage portion that stores the culture solution for the cell, together with the first member.

Effects of the Invention

According to the first aspect to third aspect of the present technology, the connection electrically connecting the cell potential detection chip and the substrate is protected, and additionally the culture solution for the cell can be stored. Particularly, according to the first aspect to third aspect of the present technology, the culture solution for the cell can be prevented from leaking.

Note that the effects herein are not necessarily limitative and thus any of the effects in the present disclosure may be provided.

MODE FOR CARRYING OUT THE INVENTION

Modes for carrying out the invention (hereinafter, referred to as "embodiments") will be described in detail below with reference to the drawings. Note that the descriptions will be given in the following order.

1. Exemplary Configuration of Cell Potential Detection Chip
2. First Embodiment (example in which a liquid-storage unit is used)
3. Second Embodiment (example in which a liquid-storage unit is provided with an overcoat)
4. Third Embodiment (example in which a ring and a liquid-storage sealing resin are used)
5. Fourth Embodiment (example in which a liquid-storage sealing resin is provided with an overcoat)
6. Fifth Embodiment (example in which a liquid-storage sealing portion has a double-layered structure)
7. Sixth Embodiment (exemplary information processing system)
8. Modifications
9. Others

1. Exemplary Configuration of Cell Potential Detection Chip

First, an exemplary configuration of a cell potential detection chip to be applied to the present technology, will be described with reference to FIGS. 1 to 3.

Figure 1:
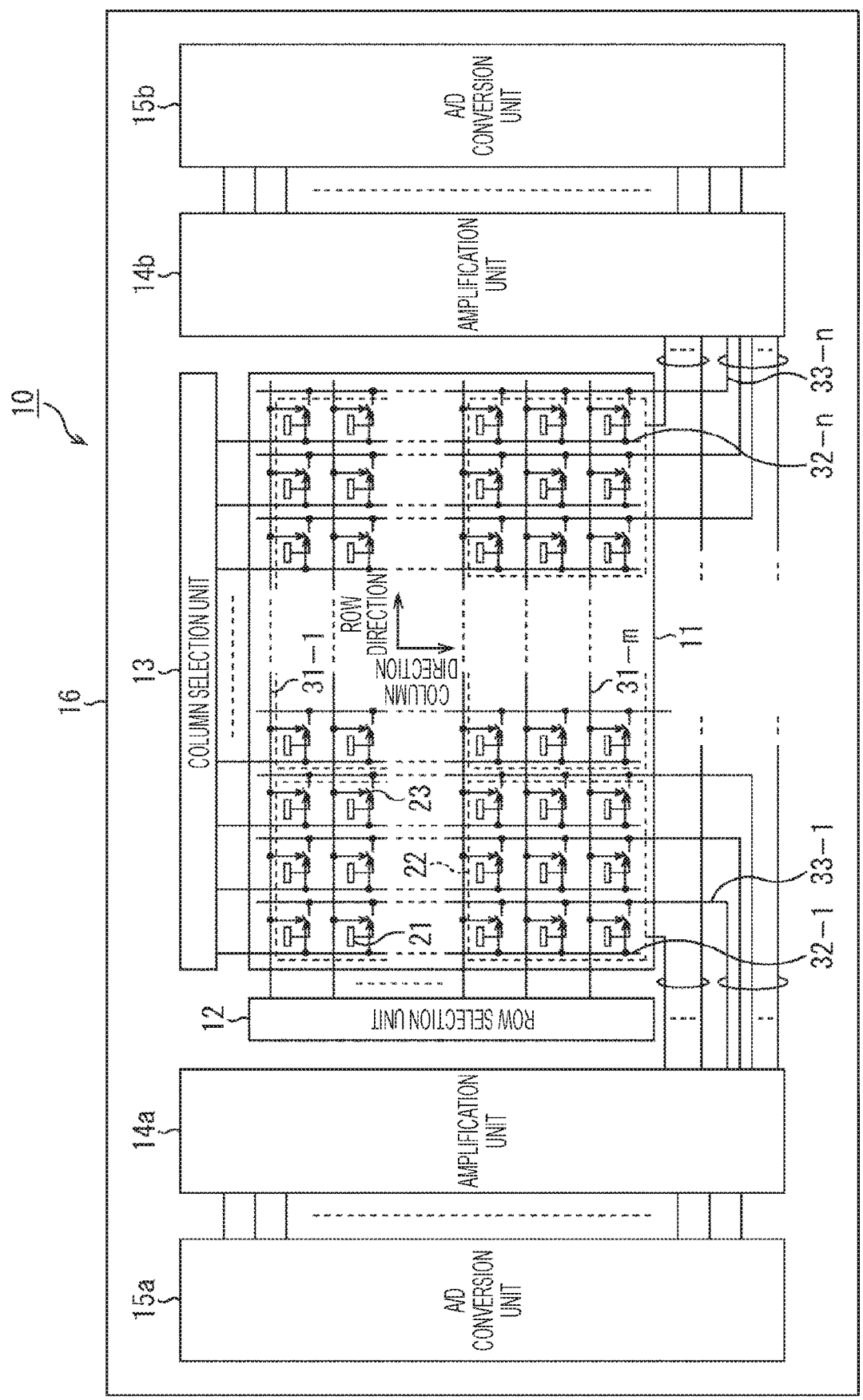
FIG. 1 schematically illustrates the configuration of a cell potential detection chip.

FIG. 1 schematically illustrates the configuration of the cell potential detection chip 10. The cell potential detection chip 10 is a device in which an electrode unit 11 created with a CMOS integrated-circuit technology, a row selection unit 12, a column selection unit 13, an amplification unit 14A, an amplification unit 14B, an A/D conversion unit 15A, and an A/D conversion unit 15B are integrated on one semiconductor substrate 16. Herein, a pair of the amplification unit 14A and the A/D conversion unit 15A and a pair of the amplification unit 14B and the A/D conversion unit 15B are disposed, respectively, on one side and the other side across the electrode unit 11. However, the pair of the amplification unit 14A and the A/D conversion unit 15A and the pair of the amplification unit 14B and the A/D conversion unit 15B can be disposed on one side of the electrode unit 11.

The electrode unit 11 includes a plurality of reading electrodes 21 that detects the potential at an action-potential source point due to a chemical change of a cell, disposed in an array of m rows by n columns. For example, the reading electrodes 21 each have an electrode size substantially the same as the size of the action-potential source point. A reference electrode 22 that detects reference potential, is disposed in the array of the reading electrodes 21.

Herein, as an example, one reference electrode 22 is disposed to a total of nine pieces of reading electrodes 21 of three rows by three columns. Furthermore, each reading electrode 21 is smaller in electrode size than the reference electrode 22 In other words, the reference electrode 22 is larger in electrode size than each reading electrode 21. The reference potential that the reference electrode 22 detects is criterial potential at the time of acquisition of the difference to the potential at the action-potential source point that each reading electrode 21 detects. The electrode structure of the reading electrodes 21 and the reference electrode 22 is planar.

For the reading electrodes 21 of m rows by n columns, row selection lines 31-1 to 31-$m$ are wired one-to-one to the rows thereof, and column selection lines 32-1 to 32-$n$ and signal reading lines 33-1 to 33-$n$ are wired one-to-one to the columns thereof. Respective one ends of the row selection lines 31-1 to 31-$m$ are connected with the corresponding row output ends of the row selection unit 12. Respective one ends of the column selection lines 32-1 to 32-$n$ are connected with the corresponding column output ends of the column selection unit 13.

The reading electrodes 21 are connected with the signal reading lines 33-1 to 33-$n$ through switches 23. In FIG. 1, although each switch 23 is illustrated as one switch for simplification of the drawing, in practice, each switch 23 includes at least two switches for row selection and for column selection. Furthermore, corresponding to this, the signal reading lines 33-1 to 33-$n$ each include at least two signal reading lines.

For the switches 23, for example, the switches for row selection are driven on (closed) by row selection signals applied from the row selection unit 12 through the row selection lines 31-1 to 31-$m$, and the switches for column selection are driven on by column selection signals applied from the column selection unit 13 through the column selection lines 32-1 to 32-$n$. When the switches for row selection and the switches for column selection are turned on, the potentials detected by the reading electrodes 21 are output to the signal reading lines 33-1 to 33-$n$. Then, the potentials are transferred to the amplification unit 14A and the amplification unit 14B through the signal reading lines 33-1 to 33-$n$.

Note that, herein, the potential reading system of the reading electrodes 21 has been mainly described. However, for the potential reading system of the reference electrodes 22, a similar configuration is provided basically. Specifically, the potential reading system including the row selection unit 12, the column selection unit 13, the row selection lines 31-1 to 31-$m$, the column selection lines 32-1 to 32-$n$, and the signal reading lines 33-1 to 33-$n$, is provided dually for potential reading of the reading electrodes 21 and for potential reading of the reference electrodes 22.

The detected potentials of the reading electrodes 21 and the detected potentials of the reference electrodes 22 read by the dual potential reading system, are supplied to the amplification unit 14A and the amplification unit 14B. The amplification unit 14A and the amplification unit 14B each include a plurality of differential amplifiers each shared between a plurality of reading electrodes 21. For example, with one reference electrode 22 as a unit, difference is acquired between the detected potential (reference potential) of a reference electrode 22 and the detected potentials of the nine pieces of reading electrodes 21 belonging to the reference electrode 22. The difference is supplied to the A/D conversion unit 15A or the A/D conversion unit 15B. The A/D conversion unit 15A performs A/D conversion to the difference output from the amplification unit 14A, and the A/D conversion unit 15B performs A/D conversion to the difference output from the amplification unit 14B. Then, the A/D conversion unit 15A and the A/D conversion unit 15B each output a detection signal having a digital value corresponding to the potentials detected by the reading electrodes 21.

According to Example 1 of the cell potential detection chip 10 having the configuration, a reference electrode 22 is disposed near a reading electrode 21, specifically, in an array of reading electrodes 21. Then, the reference electrode 22 is larger in size than the reading electrode 21. As the reference electrode 22, various electrodes in shape can be used. FIG. 2 illustrates an example in which the electrode shape of the reference electrode 22 is square.

Figure 2:
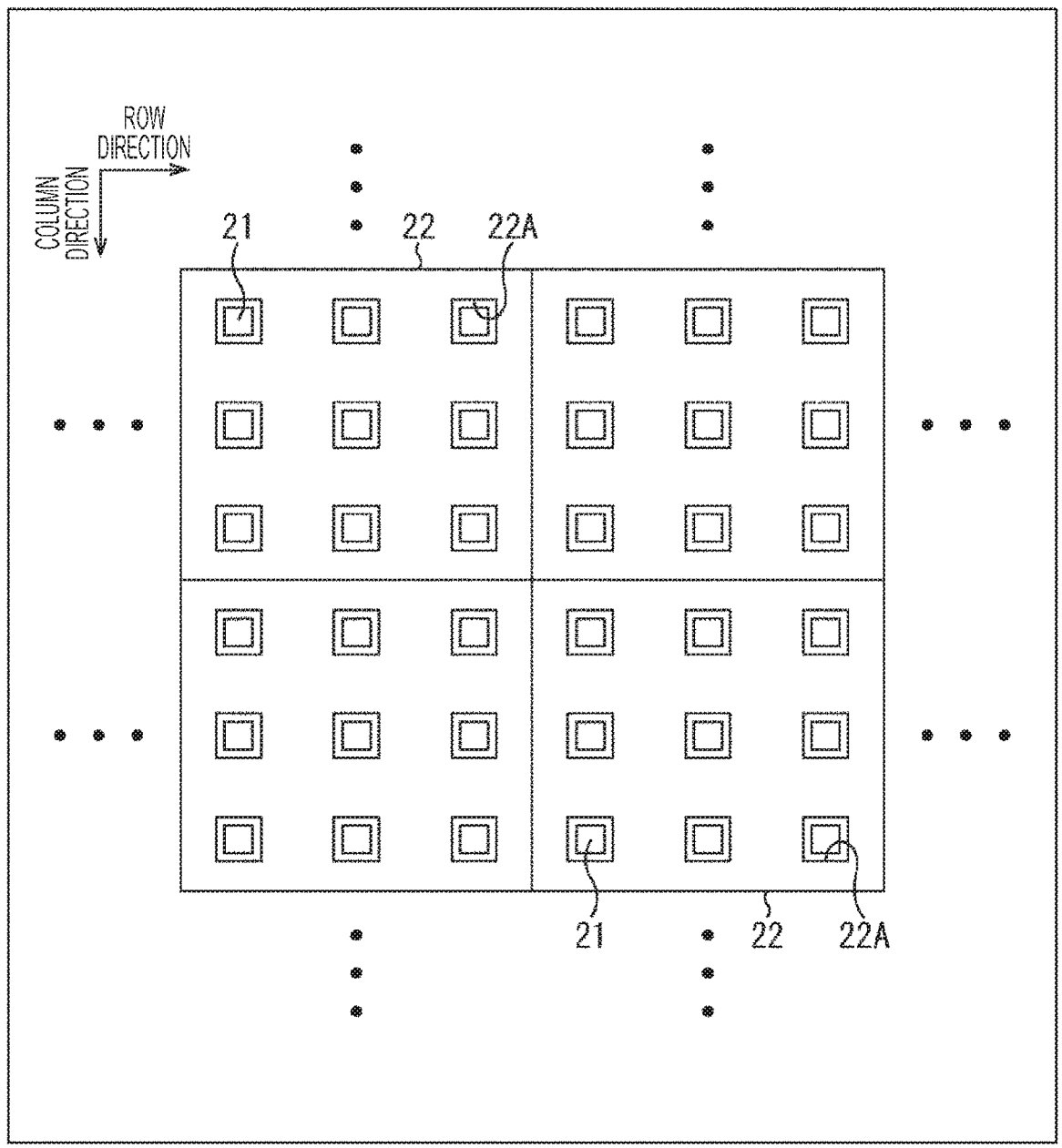
FIG. 2 is a plan view of an exemplary electrode arrangement of reference electrodes and reading electrodes.

Because of the correspondence relationship with FIG. 1, FIG. 2 exemplifies a reference electrode 22 disposed with a total of nine pieces of reading electrodes 21 of three rows by three columns as a unit. One reference electrode 22 has nine openings 22A corresponding in position to nine pieces of reading electrodes 21 disposed in a matrix, in the plane thereof. Then, the reference electrode 22 is disposed such that the nine pieces of reading electrodes 21 disposed in a matrix are located in the nine openings 22A, respectively. In other words, the reading electrodes 21 are disposed, respectively, in the openings 22A of the reference electrode 22.

The electrode arrangement of reading electrodes 21 and reference electrodes 22 as illustrated in FIG. 2 is suitable for reading of a local change in potential. As an example, for reading of the action potential of a living cell that is approximately 5 μm in size (hereinafter, simply referred to as potential), a reading electrode 21 that is approximately 5 μm in electrode size and a reference electrode 22 that is ten times or more as large as the reading electrode 21, namely, 50 μm or more in electrode size, are disposed.

In such a case, a portion at which the action potential occurs is equivalent to one local point. The potential varies approximately tenfold between the reading electrode 21 that is 5 μm in size and the reference electrode 22 that is 50 μm in size. Then, acquisition of the difference between the potential detected by the reading electrode 21 and the potential detected by the reference electrode 22, enables measurement of the action potential of the living cell.

Figure 3:
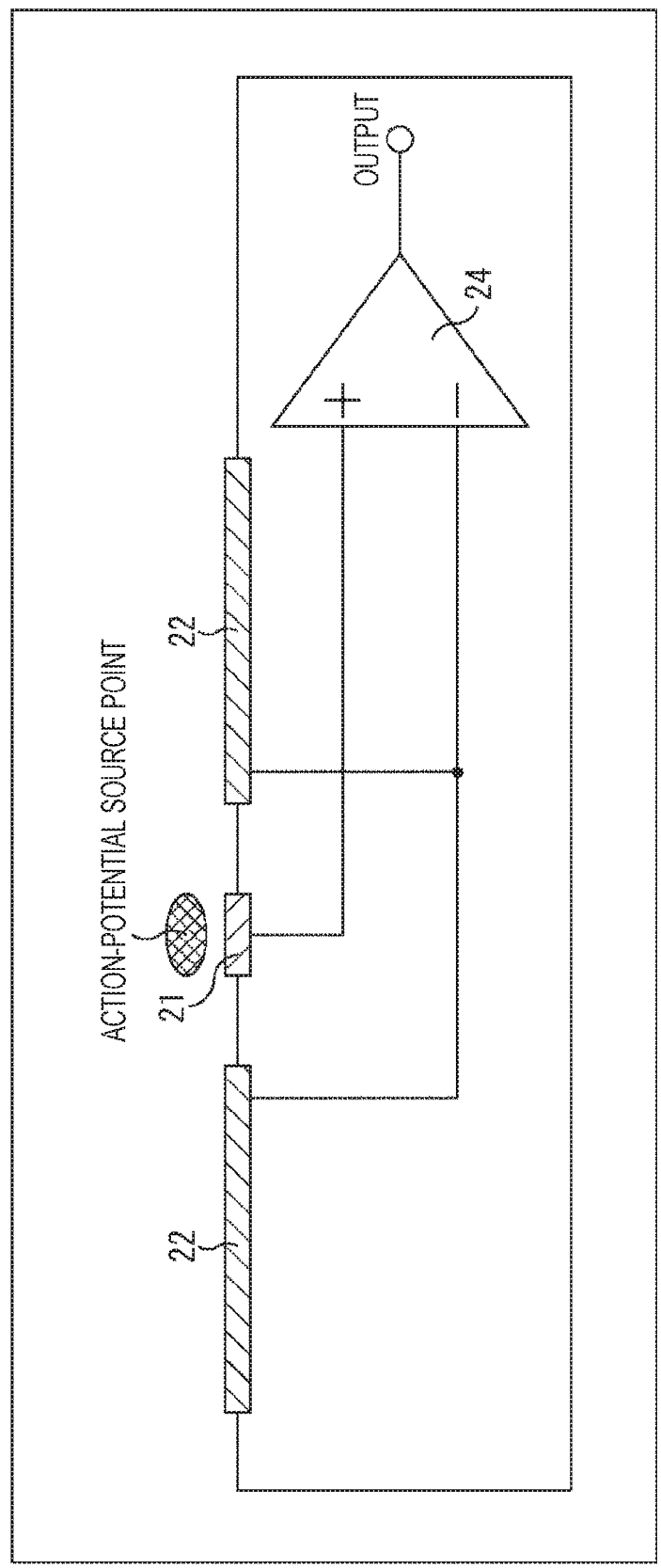
FIG. 3 is a schematic view of an exemplary wiring structure between a reading electrode and a reference electrode, and a differential amplifier.

FIG. 3 illustrates exemplary wiring between a reading electrode 21 and a reference electrode 22, and one differential amplifier from the amplification unit 14A or the amplification unit 14B. As described above, adoption of the configuration in which a reference electrode 22 is disposed near a reading electrode 21, more specifically, in an array of reading electrodes 21, enables the reading electrode 21 and the reference electrode 22 to be equal in position with respect to the differential amplifier 24. Therefore, two lines of wiring connecting the reading electrode 21 and the reference electrode 22, and two input ends of the differential amplifier 24, are electrically almost equivalent in wiring capacitance and environmental capacitance. Thus, respective noises to be superimposed on the lines of wiring can be made equal, so that noise can be inhibited from being involved in an output of the differential amplifier 24 at the time of acquisition of the difference therebetween.

2. First Embodiment

Next, a first embodiment of the present technology will be described with reference to FIGS. 4 to 6.

<Exemplary Configuration of Cell Potential Detection Device>

Figure 4:
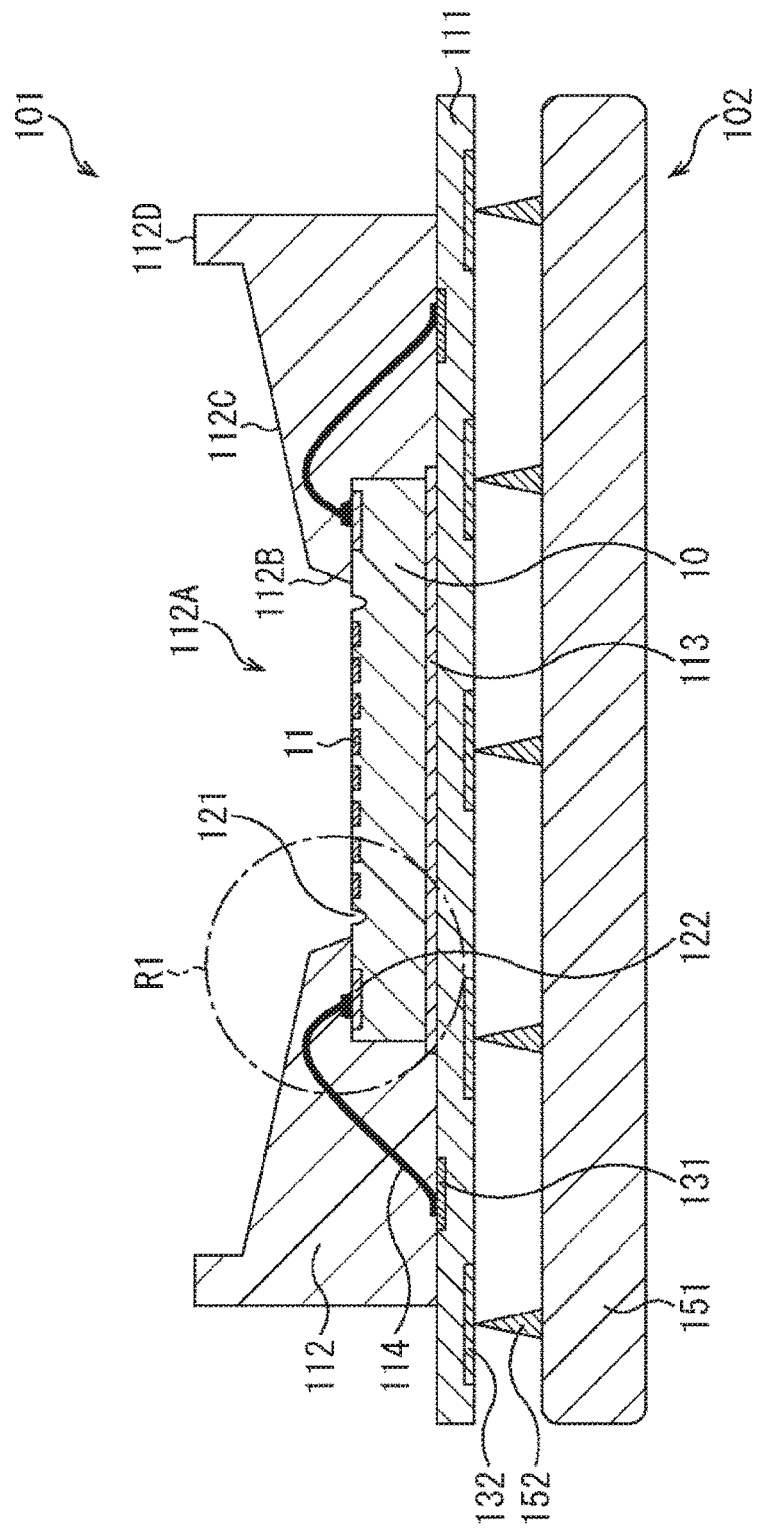
FIG. 4 is a schematic sectional view of a cell potential detection device according to a first embodiment.

FIG. 4 is a schematic sectional view of a cell potential detection device 101 according to the first embodiment of the present technology. FIG. 5 is a schematic plan view of the cell potential detection device 101.

The cell potential detection device 101 is a semiconductor module in which a cell potential detection chip 10 is packaged. The cell potential detection device 101 includes the cell potential detection chip 10, a substrate 111, and a liquid-storage unit 112.

The cell potential detection chip 10 is bonded at a substantially center of a predetermined face of the substrate 111 (hereinafter, referred to as a component face) through a die bonding paste 113.

A grooved slit dam 121 surrounding the periphery of an electrode unit 11, is formed on a face of the cell potential detection chip 10 on which the electrode unit 11 is disposed (hereinafter, referred to as a detection face). For example, at the time of formation of the liquid-storage unit 112, the slit dam 121 inhibits a resin for forming the liquid-storage unit 112 from flowing into the electrode unit 11. Note that no slit dam 121 is illustrated in FIG. 5.

A plurality of pads 122 is disposed on the periphery of the slit dam 121 such that the periphery of the electrode unit 11 is surrounded by the plurality of pads 122.

A plurality of pads 131 is disposed on the component face of the substrate 111 such that the plurality of pads 131 surrounds the periphery of the cell potential detection chip 10. The pads 122 of the cell potential detection chip 10 correspond one-to-one to the pads 131 of the substrate 111. The pads 122 are each connected with the corresponding pad 131 through a wire 114.

A plurality of circular external terminals 132 is disposed in a grid pattern on the opposite face to the component face of the substrate 111 (hereinafter, referred to as a back face). Furthermore, each external terminal 132 is subjected to Au plating so as not to corrode. For example, the external terminals 132 are connected, respectively, with pins 152 provided at a mount 151 of a socket 102. Then, the cell potential detection device 101 is electrically connected to external equipment through the socket 102, and outputs, for example, a detection signal indicating a result of detection of the potential of a cell, to the external equipment.

The liquid-storage unit 112 has a function of storing culture solution for culturing a disposed cell and a function of sealing and protecting a connection electrically connecting the cell potential detection chip 10 and the substrate 111 (hereinafter, referred to as an electric connection).

Specifically, a rectangular opening 112A is formed at the center of the liquid-storage unit 112. The opening 112A ranges over the periphery of the slit dam 121 on the detection face of the cell potential detection chip 10, so that the electrode unit 11 is exposed outward through the opening 112A.

The periphery of the opening 112A is surrounded by an inclined face 112B. The inner circumference of the inclined face 112B is in contact with the detection face of the cell potential detection chip 10. The inclined surface 112B inclines upward from the inner circumference to the outer circumference thereof. The periphery of the inclined face 112B is surrounded by an inclined face 112C. From the inclined face 112B, the inclined face 112C inclines gradually upward from the inner circumference to the outer circumference thereof. The inclined face 112B and the inclined face 112C form a liquid-contact face to be in contact with the culture solution. The periphery of the inclined face 112C is surrounded by a vertical wall 112D.

Therefore, formed is a substantially rectangularly-dished liquid-storage portion peripherally surrounded by the inclined face 112B, the inclined face 112C, and the inner wall of the wall 112D, having a bottom face that is an exposed portion including the electrode unit 11, exposed through the opening 112A on the detection face of the cell potential detection chip 10. Storage of the culture solution in the liquid-storage portion enables immersion of the cell disposed on the electrode unit 11, in the culture solution for culturing.

Note that, in order not to damage the cell, a harmless stabilizer including no ingredient harmful to the cell is used for the liquid-storage unit 112. For example, epoxy resin or silicone resin is used for the liquid-storage unit 112.

The side face of the liquid-storage unit 112 stands vertically to the component face of the substrate 111, outside the pads 131 on the component face of the substrate 111. Then, the periphery of the electrode unit 11 (exposed portion) on the detection face of the cell potential detection chip 10 and the periphery of the cell potential detection chip 10 on the component face of the substrate 111, are sealed by the liquid-storage unit 112. Therefore, the liquid-storage unit 112 seals the electric connection including the pads 122 of the cell potential detection chip 10, the pads 131 of the substrate 111, and the wires 114 each connecting the pad 122 and the pad 131 corresponding mutually.

Figure 5:
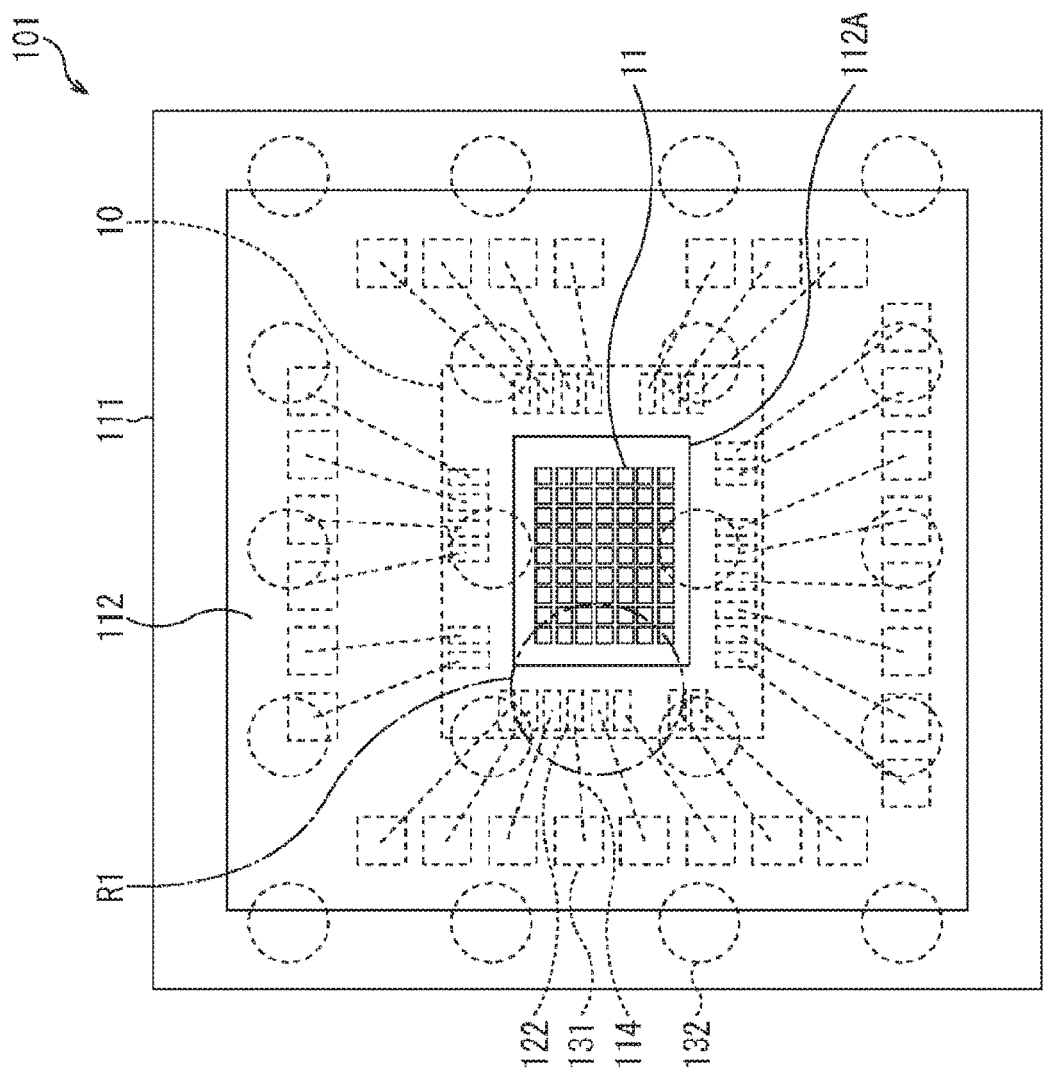
FIG. 5 is a schematic plan view of the cell potential detection device according to the first embodiment.
Figure 6:
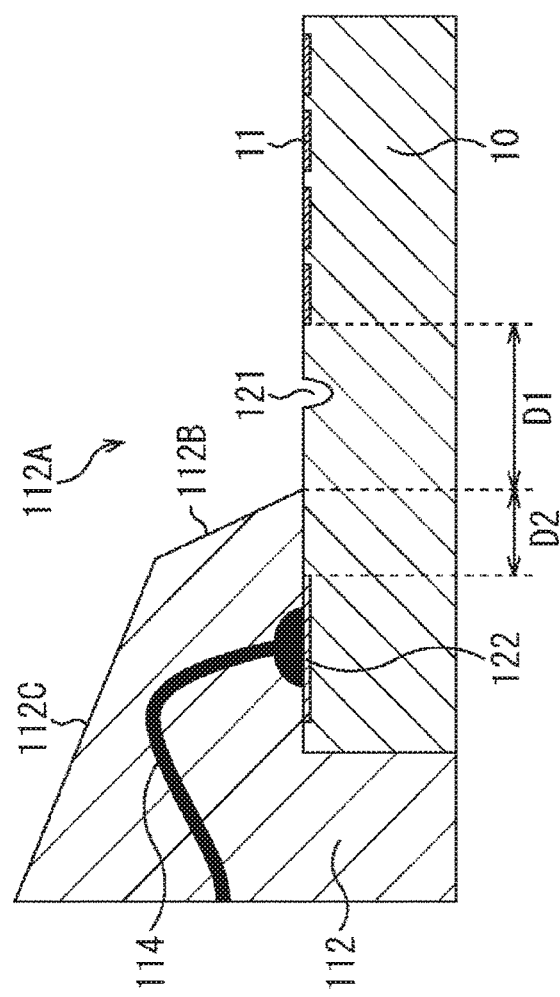
FIG. 6 is an enlarged view of an end portion of a cell potential detection chip of the cell potential detection device of FIG. 4.

FIG. 6 is an enlarged view of the inside of a region R1 surrounded by a dot-and-dash line of FIGS. 4 and 5.

For example, the distance D1 between the outer circumference of the electrode unit 11 and the inner circumference of the liquid-storage unit 112 (outer circumference of the opening 112A), is set to 100 μm or more. Furthermore, for example, the distance D2 between the inner circumference of the liquid-storage unit 112 and the side on the electrode unit 11 side of the pad 122, is set to 50 μm or more.

Provision of the liquid-storage unit 112 as above enables the cell to be cultured with storage of a necessary amount of culture solution regardless of the size of the cell. Furthermore, the liquid-storage unit 112 can seal and protect the electric connection between the cell potential detection chip 10 and the substrate 111. Moreover, the liquid-storage unit 112 having the function of storing the culture solution and the function of sealing the electric connection between the cell potential detection chip 10 and the substrate 111, enables reduction in the number of components and improvement in productivity.

3. Second Embodiment

Next, a second embodiment of the present technology will be described with reference to FIGS. 7 to 10.

<Exemplary Configuration of Cell Potential Detection Device>

Figure 7:
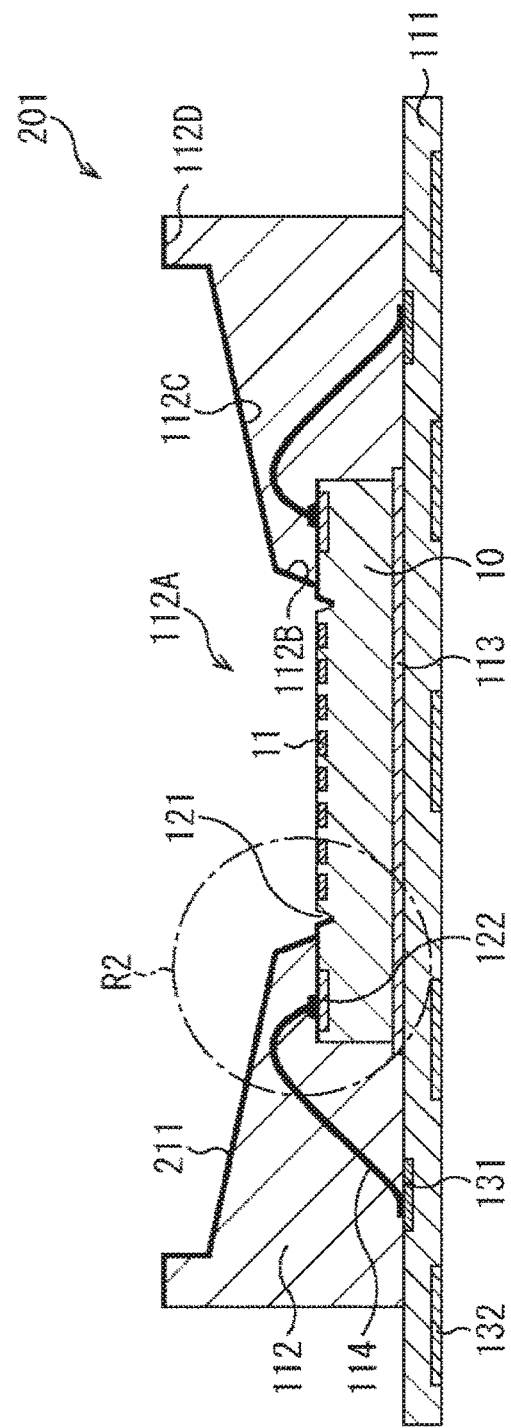
FIG. 7 is a schematic sectional view of a cell potential detection device according to a second embodiment.

FIG. 7 is a schematic sectional view of a cell potential detection device 201 according to the second embodiment of the present technology. Note that, in the figure, parts corresponding to those of the cell potential detection device 101 of FIG. 4 are denoted with the same reference signs.

The cell potential detection device 201 is different from the cell potential detection device 101 in that an overcoat 211 is formed.

In a case where culture solution is stored in a liquid-storage portion of the cell potential detection device 201, the overcoat 211 covers at least a face of a liquid-storage unit 112 in contact with the culture solution. Specifically, the overcoat 211 covers an inclined face 121B, an inclined face 121C, and the inner wall of a wall 121D of the liquid-storage unit 112. Note that, in the example, the overcoat 211 covers the upper face of the wall 121D, the part between the outer circumference of an opening 112A and a slit dam 121, and the slant from the outer circumference to the bottom of the slit dam 121.

In order not to damage a cell, the overcoat 211 includes a harmless thin film including no ingredient harmful to the cell. For example, a thin film of silicon oxide ($SiO_2$), silicon oxynitride (SiON), aluminum oxide ($Al_2O_3$), epoxy resin, silicone resin, or the like, having a thickness of approximately 10 to 1000 nm, is used for the overcoat 211. Note that the overcoat 211 may be a multilayer film in which a plurality of thin films is layered. Furthermore, there is no problem with the overcoat 211 having a thickness of 1000 nm or more.

Figure 8:
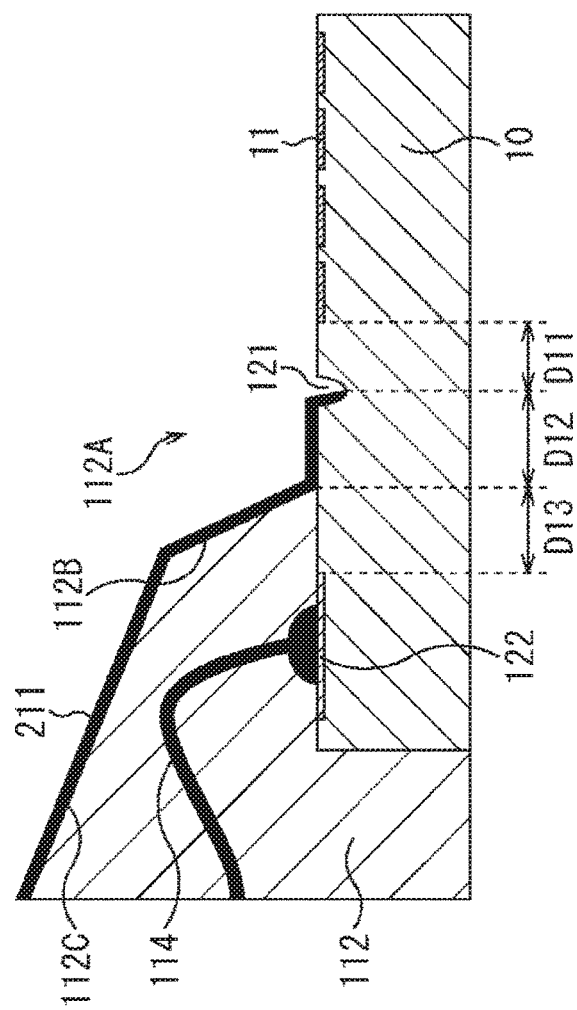
FIG. 8 is an enlarged view of an end portion of a cell potential detection chip of the cell potential detection device of FIG. 7.

FIG. 8 is an enlarged view of the inside of a region R2 surrounded by a dot-and-dash line of FIG. 7.

For example, the distance D11 between the outer circumference of an electrode unit 11 and the inner circumference of the overcoat 211, is set to 50 μm or more. For example, the distance D12 between the inner circumference of the overcoat 211 and the inner circumference of the liquid-storage unit 112 (outer circumference of the opening 112A), is set to 50 μm or more. For example, the distance D13 between the inner circumference of the liquid-storage unit 112 and the side on the electrode unit 11 side of a pad 122, is set to 50 μm or more, similarly to the distance D2 of FIG. 6.

<Method of Manufacturing Cell Potential Detection Device>

Next, a method of manufacturing the cell potential detection device 201 will be described with reference to FIGS. 9 and 10. Note that, in the figures, parts unnecessary to the description are appropriately denoted with no reference sings. Furthermore, no external terminal 132 of a substrate 111 is illustrated.

In a lift-off process before process P1, for each of a plurality of cell potential detection chips 10 formed on a semiconductor wafer (not illustrated), a resist 251 is formed such that the resist 251 covers the electrode unit 11. Then, each cell potential detection chip 10 is singulated.

In process P1, a singulated cell potential detection chip 10 is bonded to the component face of the substrate 111 through a die bonding paste 113 (die bonding).

In process P2, wire bonding is performed. That is pads 122 of the cell potential detection chip 10 and pads 131 of the substrate 111 are connected through wires 114, respectively. In this case, for example, a collet is used to prevent foreign substances from coming in contact with the resist 251.

In process P3, the liquid-storage unit 112 is formed by injection molding. For example, with a method similar to a molding process, a resin for forming the liquid-storage unit 112 is poured in a mold and then is cured. Therefore, the liquid-storage unit 112 is formed, resulting in sealing of the periphery of the electrode unit 11 on the detection face of the cell potential detection chip 10 and the periphery of the cell potential detection chip 10 on the component face of the substrate 111. In this case, the slit dam 121 prevents the resin from flowing into the electrode unit 11.

In process P4, the overcoat 211 is formed on the surface of the cell potential detection device 201. As the method of forming the overcoat 211, for example, vapor deposition, electrostatic coating, inkjet coating, or the like is used. In this case, the resist 251 prevents the overcoat 211 from adhering to the electrode unit 11. Note that the overcoat 211 may adhere to the side face of the liquid-storage unit 112 and the component face of the substrate 111.

In process P5, the resist 251 is removed by wet etching. Therefore, the electrode unit 11 is exposed outward.

Note that, in process P1, the plurality of cell potential detection chips 10 may be bonded on an aggregate board, and then, in process P5, each cell potential detection device 201 may be singulated after simultaneous removal of the respective resists 251 of the cell potential detection chips 10.

In the manner, the cell potential detection device 201 is manufactured.

Provision of the overcoat 211 to the cell potential detection device 201 as above, enables a member including an ingredient harmful to the cell, to be used for the liquid-storage unit 112.

Furthermore, for example, use of inorganic material for the overcoat 211 enables sterilization treatment or disinfection treatment of the cell potential detection device 201 by flaming.

4. Third Embodiment

Next, a third embodiment of the present technology will be described with reference to FIGS. 11 and 12.

<Exemplary Configuration of Cell Potential Detection Device>

Figure 11:
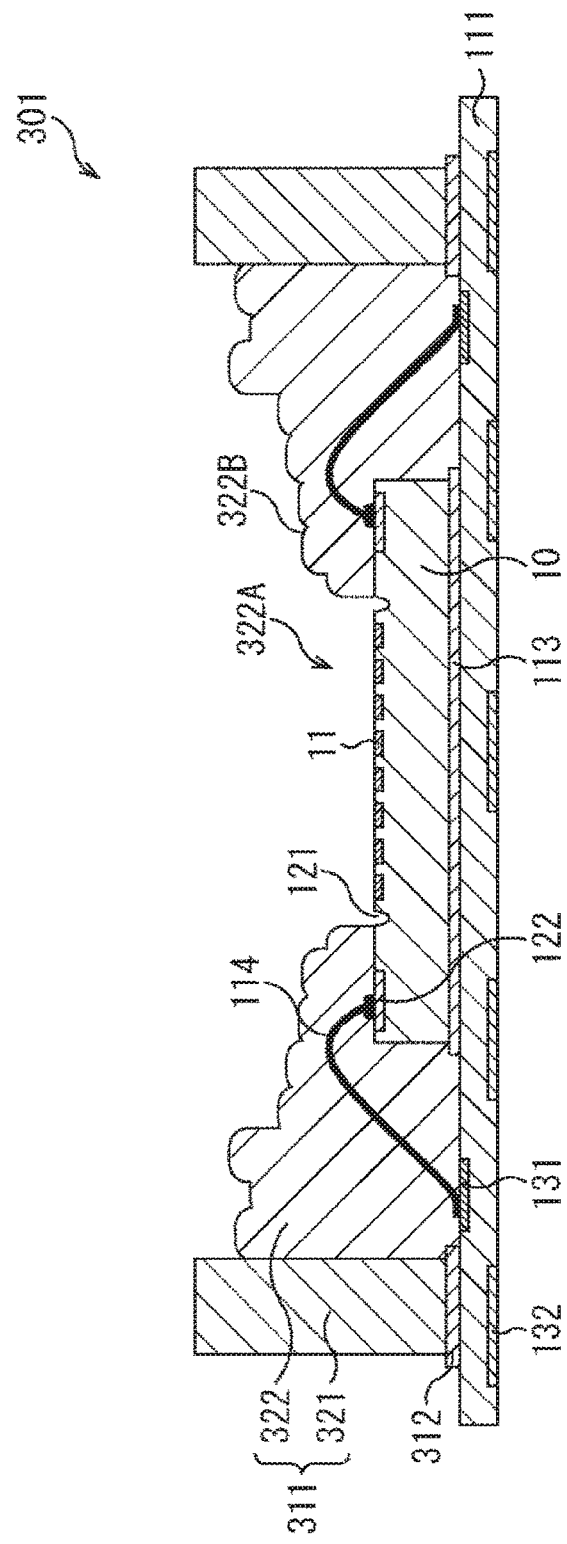
FIG. 11 is a schematic sectional view of a cell potential detection device according to a third embodiment.
Figure 12:
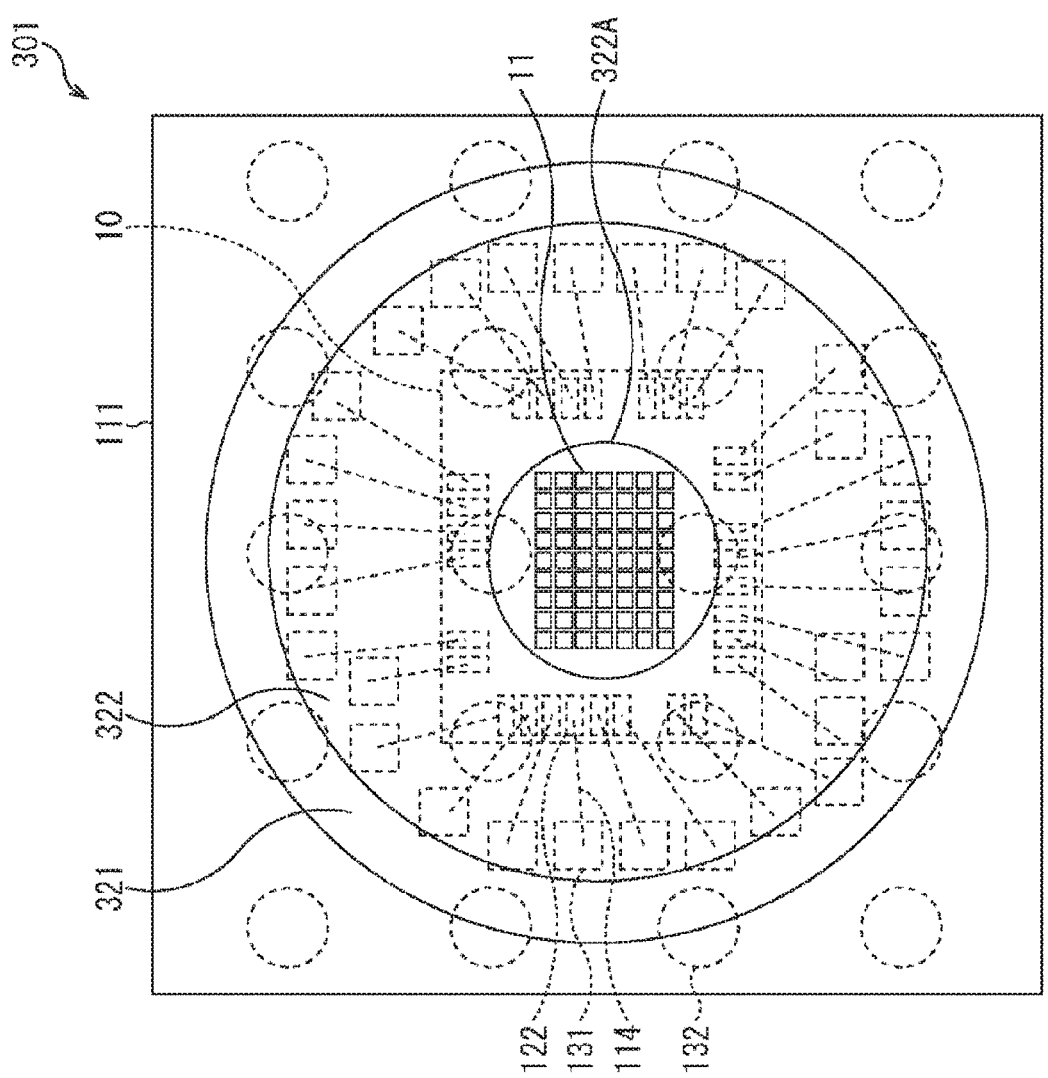
FIG. 12 is a schematic plan view of the cell potential detection device according to the third embodiment.

FIG. 11 is a schematic sectional view of a cell potential detection device 301 according to the third embodiment of the present technology. FIG. 12 is a schematic plan view of the cell potential detection device 301. Note that, in the figures, parts corresponding to those of the cell potential detection device 101 of FIGS. 4 and 5 are denoted with the same reference signs.

The cell potential detection device 301 is different from the cell potential detection device 101 in that a liquid-storage sealing portion 311 is provided instead of the liquid-storage unit 112.

The liquid-storage sealing portion 311 has a function of storing culture solution and a function of sealing and protecting the electric connection between a cell potential detection chip 10 and a substrate 111, similarly to the liquid-storage unit 112 of the cell potential detection device 101. The liquid-storage sealing portion 311 includes a ring 321 and a liquid-storage sealing resin 322.

The ring 321 that is cylindrical and includes glass, is bonded to the component face of the substrate 111 through a seal resin 312. The outer wall of the ring 321 surrounds the outside of a region in which pads 131 of the substrate 111 are disposed. That is all the pads 131 are disposed in the region surrounded by the outer wall of the ring 321. Note that part of the ring 321 may overlap part of the pads 131. Note that the inner wall of the ring 321 is disposed outside the bonded portion of each pad 131 with a wire 114. That is the bonded portions of all the pads 131 with the wires 114 are disposed in the region surrounded by the inner wall of the ring 321. Note that a member different from glass can be used for the ring 321.

The liquid-storage sealing resin 322 is poured between the outer circumference of a slit dam 121 on the detection face of the cell potential detection chip 10 and the inner wall of the ring 321. The liquid-storage sealing resin 322 seals and protects the electric connection between the cell potential detection chip 10 and the substrate 111.

Furthermore, a circular opening 322A is formed at the center of the liquid-storage sealing resin 322. The opening 322A ranges over the outer circumference of the slit dam 121, so that an electrode unit 11 is exposed outward through the opening 322A.

The periphery of the opening 322A is surrounded by an inclined face 322B. The inner circumference of the inclined face 322B is in contact with the detection face of the cell potential detection chip 10. Furthermore, although the surface of the inclined face 112B is uneven, the inclined face 112B inclines gradually upward from the inner circumference to the outer circumference thereof. The outer circumference of the inclined face 322B is lower than the ring 321. In other words, the outer circumference of the inclined face 322B is surrounded by the wall of the ring 321. The inclined face 322B forms a liquid-contact face to be in contact with the culture solution.

Then, formed is a substantially circularly-dished liquid-storage portion peripherally surrounded by the inclined face 322B and the inner wall of the ring 321, having a bottom face that is an exposed portion including the electrode unit 11, exposed through the opening 322A on the detection face of the cell potential detection chip 10. Storage of the culture solution in the liquid-storage portion enables immersion of the cell disposed on the electrode unit 11, in the culture solution for culturing.

Note that a member similar to that of the liquid-storage unit 112 of the cell potential detection device 101 of FIG. 4 is used for the liquid-storage sealing resin 322.

5. Fourth Embodiment

Figure 14:
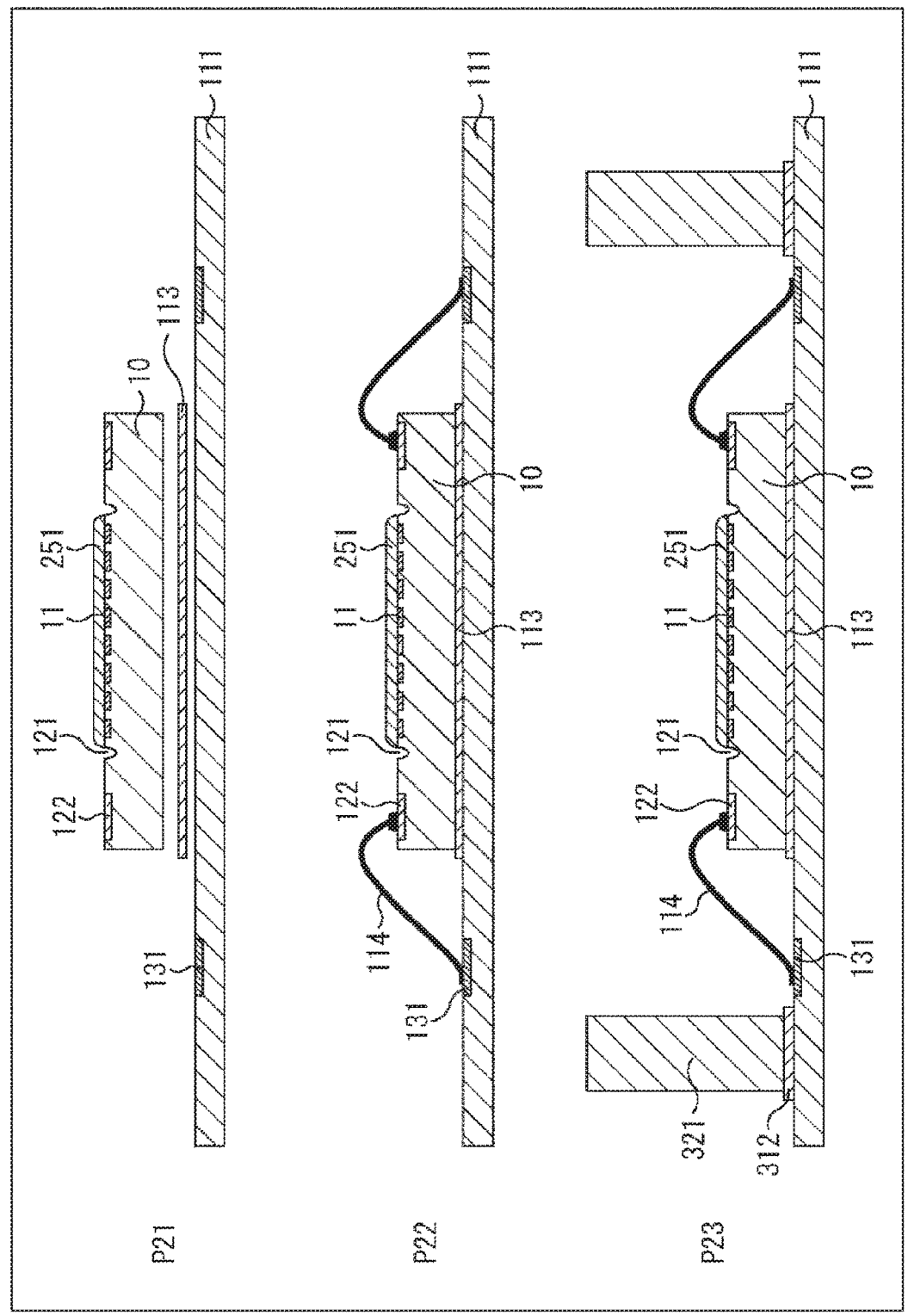
FIG. 14 explanatorily illustrates a method of manufacturing the cell potential detection device of FIG. 13.
Figure 15:
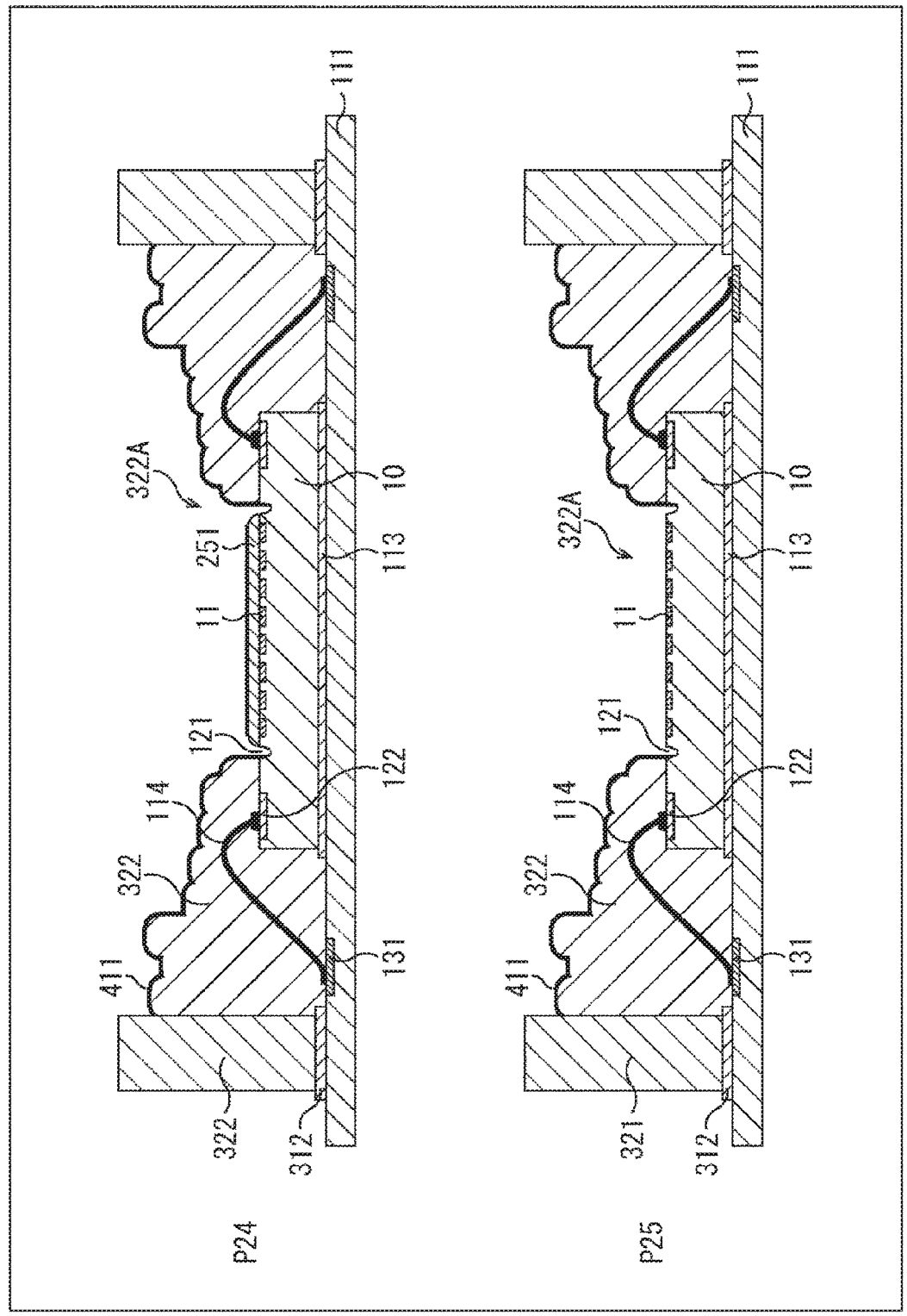
FIG. 15 explanatorily illustrates the method of manufacturing the cell potential detection device of FIG. 13.

Next, a fourth embodiment of the present technology will be described with reference to FIGS. 13 to 15.

<Exemplary Configuration of Cell Potential Detection Device>

Figure 13:
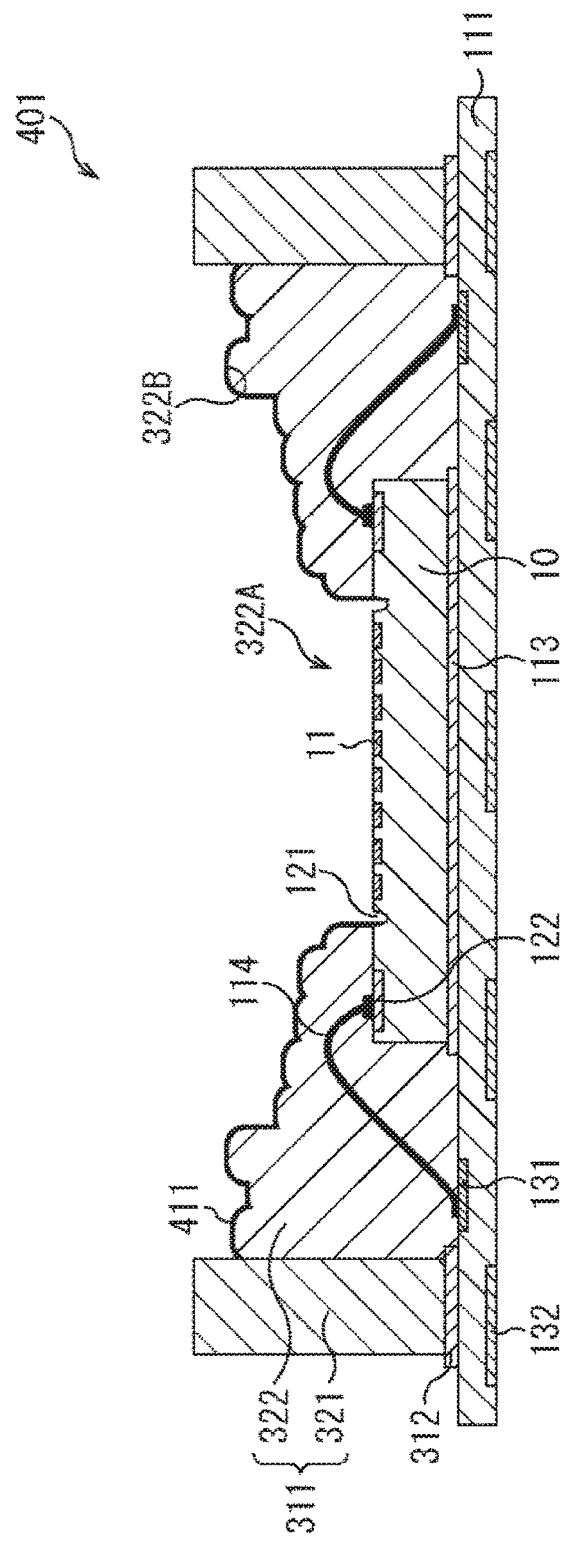
FIG. 13 is a schematic sectional view of a cell potential detection device according to a fourth embodiment.

FIG. 13 is a schematic sectional view of a cell potential detection device 401 according to the fourth embodiment of the present technology. Note that, in the figure, parts corresponding to those of the cell potential detection device 301 of FIG. 11 are denoted with the same reference signs.

The cell potential detection device 401 is different from the cell potential detection device 301 in that an overcoat 411 is formed.

In a case where culture solution is stored in a liquid-storage portion of the cell potential detection device 401, the overcoat 411 covers at least a face of a liquid-storage sealing resin 322 in contact with the culture solution. Specifically, the overcoat 411 covers an inclined face 322B of the liquid-storage sealing resin 322. Note that, in the example, the overcoat 411 covers the slant from the outer circumference to the bottom of a slit dam 121.

A film similar to that of the overcoat 211 of the cell potential detection device 301 of FIG. 7 is used for the overcoat 411.

Provision of the overcoat 411 as above enables a member including an ingredient harmful to the cell, to be used for the liquid-storage sealing resin 322.

<Method of Manufacturing Cell Potential Detection Device>

Next, a method of manufacturing the cell potential detection device 401 will be described with reference to FIGS. 14 and 15. Note that, in the figures, parts unnecessary to the description are appropriately denoted with no reference sings. Furthermore, no external terminal 132 of a substrate 111 is illustrated.

Figure 9:
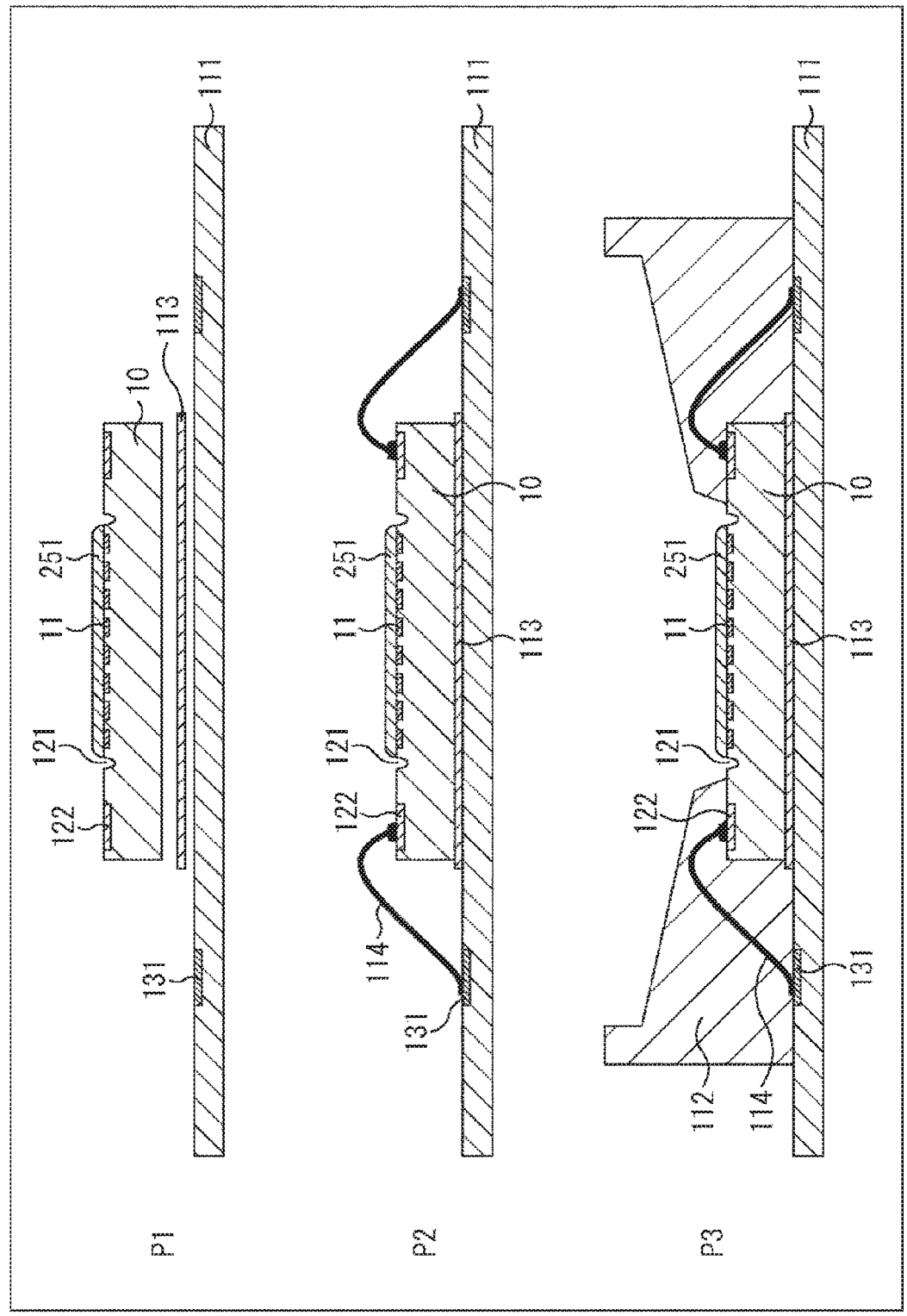
FIG. 9 explanatorily illustrates a method of manufacturing the cell potential detection device of FIG. 7.

Process P21 and process P22 are similar to process P1 and process P2 of FIG. 9, respectively. That is a cell potential detection chip 10 is bonded to the component face of the substrate 111 and then pads 122 of the cell potential detection chip 10 and pads 131 of the substrate 111 are connected through wires 114, respectively.

In process P23, a ring 321 is secured to the substrate 111. Specifically, a seal resin 312 is applied to the part to which the ring 321 is to be bonded, on the component face of the substrate 111. Then, the ring 321 is bonded onto the seal resin 312. Next, curing is performed such that the seal resin 312 is cured, so that the ring 321 is secured on the substrate 111.

In process P24, resin dispensing (applying) or resin potting (injecting) is performed to the periphery of an electrode unit 11 of the cell potential detection chip 10 inside the ring 321, resulting in formation of the liquid-storage sealing resin 322. In this case, the slit dam 121 prevents the resin from flowing into the electrode unit 11. Next, the overcoat 411 is formed on the surface of the cell potential detection device 401 by processing similar to that of process P4 of FIG. 10. Note that the overcoat 411 may adhere to the ring 321 and the component face of the substrate 111.

Figure 10:
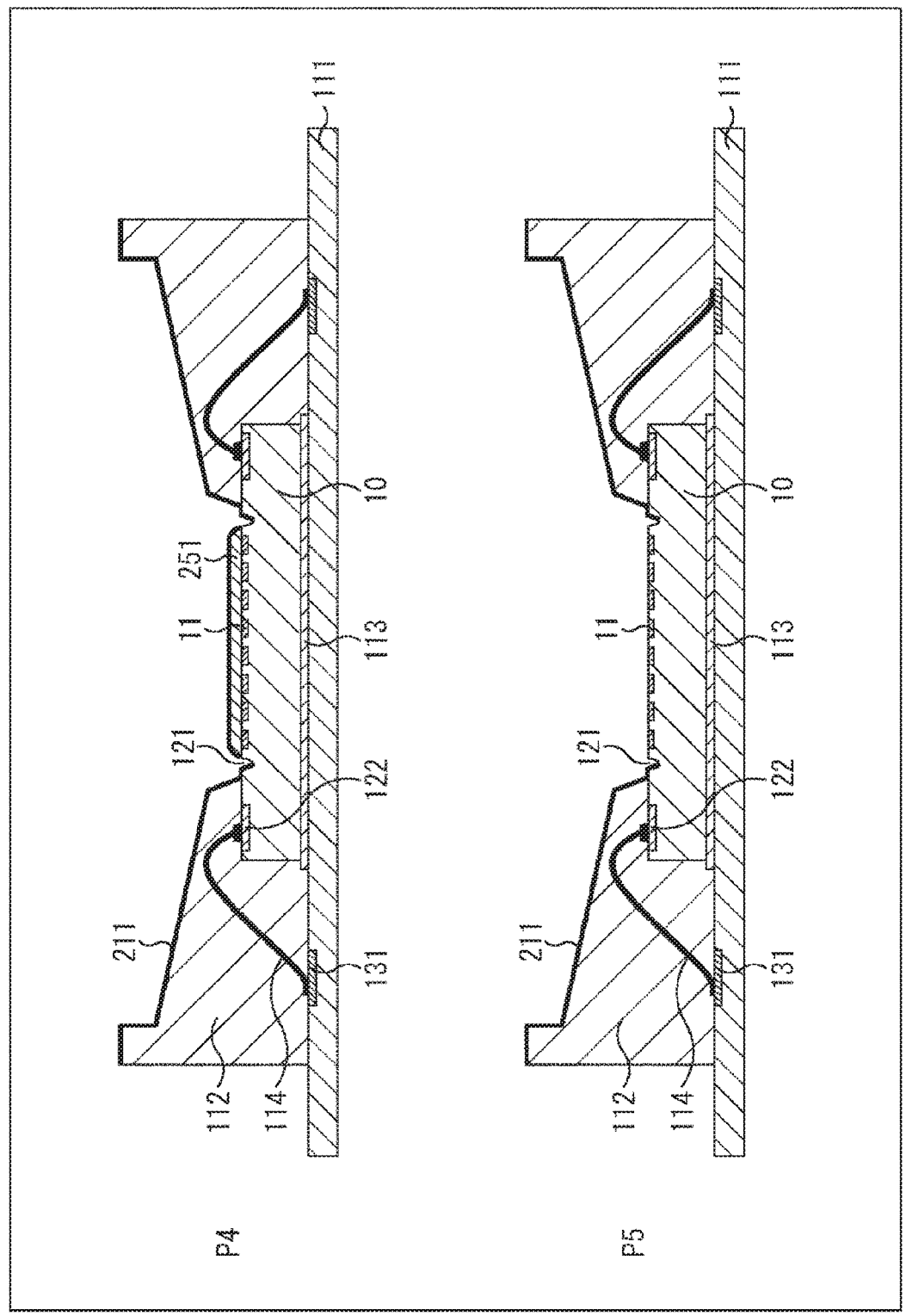
FIG. 10 explanatorily illustrates the method of manufacturing the cell potential detection device of FIG. 7.

In process P25, a resist 251 is removed by processing similar to that of process P5 of FIG. 10.

In the manner, the cell potential detection device 401 is manufactured.

Provision of the overcoat 411 to the cell potential detection device 401 as above, enables a member including an ingredient harmful to the cell, to be used for the liquid-storage sealing resin 322.

Furthermore, for example, use of inorganic material for the overcoat 411 enables sterilization treatment or disinfection treatment of the cell potential detection device 401 by flaming.

6. Fifth Embodiment

Next, a fifth embodiment of the present technology will be described with reference to FIGS. 16 to 21.

Typically, before measurement of the potential of the cell, the cell potential detection device 101 or the cell potential detection device 201 is subjected to sterilization treatment or disinfection treatment. In this case, use of autoclave (high-pressure cleaning) treatment enables automation of sterilization treatment or disinfection treatment.

However, in a case where the autoclave treatment is applied to the cell potential detection device 101 or the cell potential detection device 201, due to the difference in the coefficient of thermal expansion between the substrate 111 and the liquid-storage unit 112, the liquid-storage unit 112 is likely to separate from the substrate 111 or a gap is likely to occur therebetween. As a result, liquid leakage is likely to occur between the liquid-storage unit 112 and the substrate 111.

Furthermore, for the cell potential detection device 301 or the cell potential detection device 401, due to a similar cause, the liquid-storage sealing resin 322 is likely to separate from the substrate 111 or a gap is likely to occur therebetween.

Therefore, for the cell potential detection devices 101 to 401, instead of the autoclave treatment, for example, alcohol cleaning, pure-water cleaning, drying, ultraviolet (UV) sterilization, or the like needs using in some cases. As a result, the workload of an operator or the number of processes increases, resulting in deterioration in productivity.

The fifth embodiment is to enable application of the autoclave treatment to a cell potential detection device.

<Exemplary Configuration of Cell Potential Detection Device>

Figure 16:
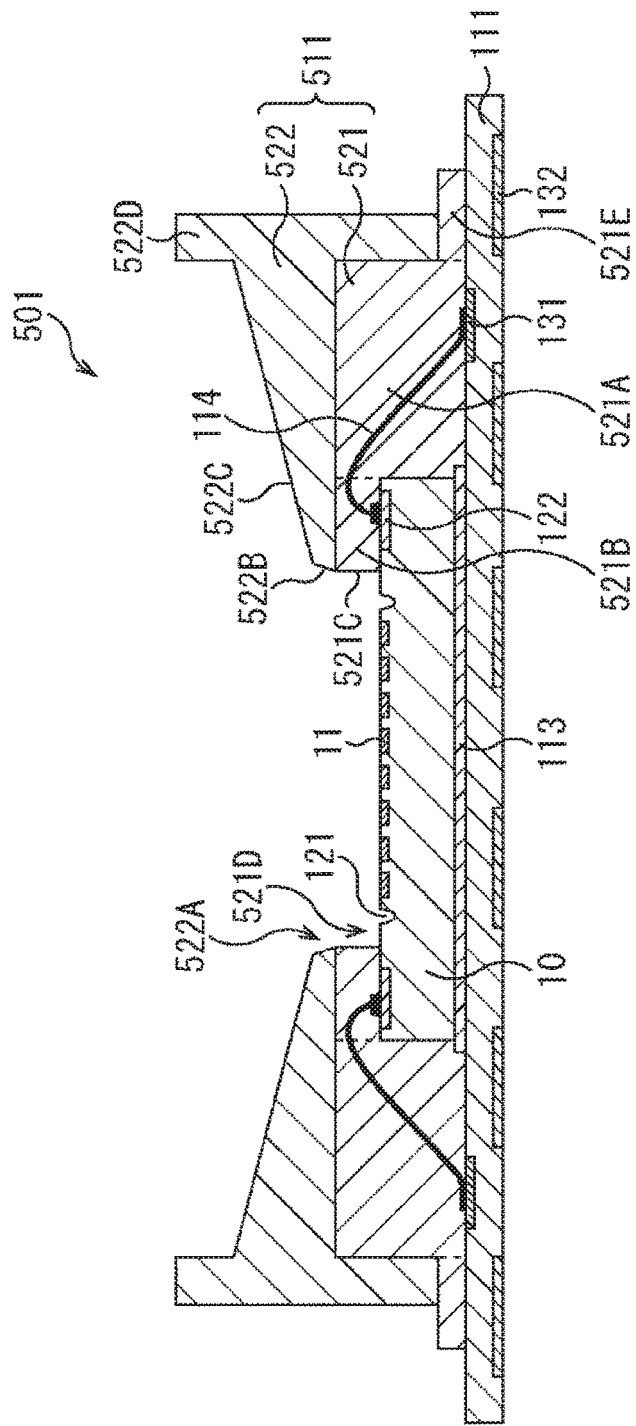
FIG. 16 is a schematic sectional view of a cell potential detection device according to a fifth embodiment.
Figure 17:
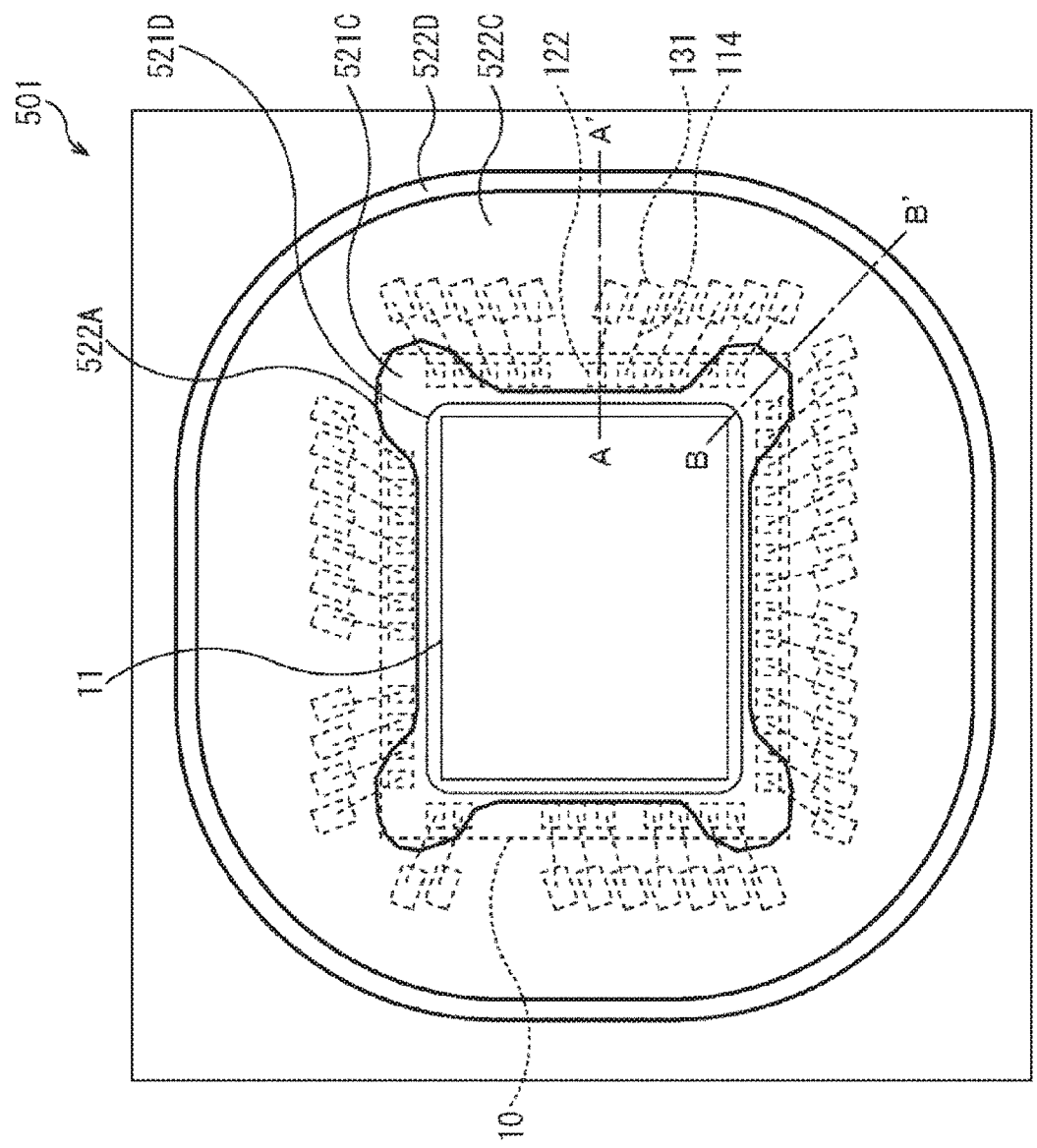
FIG. 17 is a schematic plan view of the cell potential detection device according to the fifth embodiment.

FIG. 16 is a schematic sectional view of a cell potential detection device 501 according to the fifth embodiment of the present technology. FIG. 17 is a schematic plan view of the cell potential detection device 501. Note that, in the figures, parts corresponding to those of the cell potential detection device 101 of FIGS. 4 and 5 are denoted with the same reference signs.

The cell potential detection device 501 is different from the cell potential detection device 101 in that a liquid-storage sealing portion 511 is provided instead of the liquid-storage unit 112.

The liquid-storage sealing portion 511 has a function of storing culture solution and a function of sealing and protecting the electric connection between a cell potential detection chip 10 and a substrate 111, similarly to the liquid-storage unit 112 of the cell potential detection device 101. The liquid-storage sealing portion 511 includes a sealing bonding portion 521 and a liquid-storage member 522, in which the sealing bonding portion 521 and the liquid-storage member 522 are layered in a double layer.

The sealing bonding portion 521 mainly has a function of sealing and protecting the electric connection between the cell potential detection chip 10 and the substrate 111 and a function of bonding and securing the liquid-storage member 522.

The sealing bonding portion 521 having a substantially quadrangular-barrel shape, seals the periphery of an electrode unit 11 on the detection face of the cell potential detection chip 10 and the periphery of the cell potential detection chip 10 on the component face of the substrate 111. Therefore, the sealing bonding portion 521 seals the electric connection including pads 122 of the cell potential detection chip 10, pads 131 of the substrate 111, and wires 114 each connecting a pad 122 and a pad 131 corresponding mutually.

Specifically, a quadrangular barrel portion 521A of the sealing bonding portion 521 covers the periphery of the cell potential detection chip 10 on the component face of the substrate 111. At the upper end of the quadrangular barrel portion 521A, a protrusion 521B protruding inward from the inner circumference of the quadrangular barrel portion 521A is formed. The protrusion 521B covers the periphery of a slit dam 121 on the detection face of the cell potential detection chip 10. An inclined face 521C having a lower end projecting with respect to an upper end, is formed on the inner circumference of the protrusion 521B. A substantially rectangular opening 521D is formed inside the inclined face 521C. The opening 521D ranges over the periphery of the slit dam 121, so that the electrode unit 11 is exposed outward through the opening 521D. At the lower end of the quadrangular barrel portion 521A, a flange 521E protruding outward from the outer circumference of the quadrangular barrel portion 521A is formed. The outer circumference of the flange 521E expands outside the pads 131 of the substrate 111 and the outer circumference of the liquid-storage member 522. The upper end of the sealing bonding portion 521 is higher than the upper ends of the wires 114. The sealing bonding portion 521 covers the pads 122 of the cell potential detection chip 10, the pads 131 of the substrate 111, and the wires 114.

The liquid-storage member 522 bonded on the sealing bonding portion 521, is secured to the cell potential detection device 501.

An opening 522A is formed at the center of the liquid-storage member 522. The opening 522A having a substantially rectangular shape slightly larger than the opening 521D of the sealing bonding portion 521, ranges over the opening 521D. Note that, as illustrated in FIG. 17, the opening 522A expands outward in a substantially arc shape near the four corners such that the space to the opening 521D is wider near the four corners than the other parts.

A substantially vertical face 522B is formed on the periphery of the opening 522A. An inclined face 522C inclining gradually upward from the inner circumference to the outer circumference thereof, is formed on the periphery of the face 522B. The face 522B and the inclined face 522C form a liquid-contact face to be in contact with the culture solution.

The periphery of the inclined face 522C is surrounded by a wall 522D extending upward and downward. When viewed from above, the wall 522D has a rectangular shape with four corners rounded. The upper end of the wall 522D is higher than the outer circumferential portion of the inclined face 522C. The inner wall of the wall 522D is in contact with the side face of the quadrangular barrel portion 521A of the sealing bonding portion 521. The lower end of the wall 522D is in contact with the upper face of the flange 521E of the sealing bonding portion 521.

Then, formed is a substantially rectangularly-dished liquid-storage portion peripherally surrounded by the inclined face 521C, the face 522B, the inclined face 522C, and the inner wall of the wall 522D, having a bottom face that is an exposed portion including the electrode unit 11, exposed through the opening 521D on the detection face of the cell potential detection chip 10. Storage of the culture solution in the liquid-storage portion enables immersion of the cell disposed on the electrode unit 11, in the culture solution for culturing.

Figure 18:
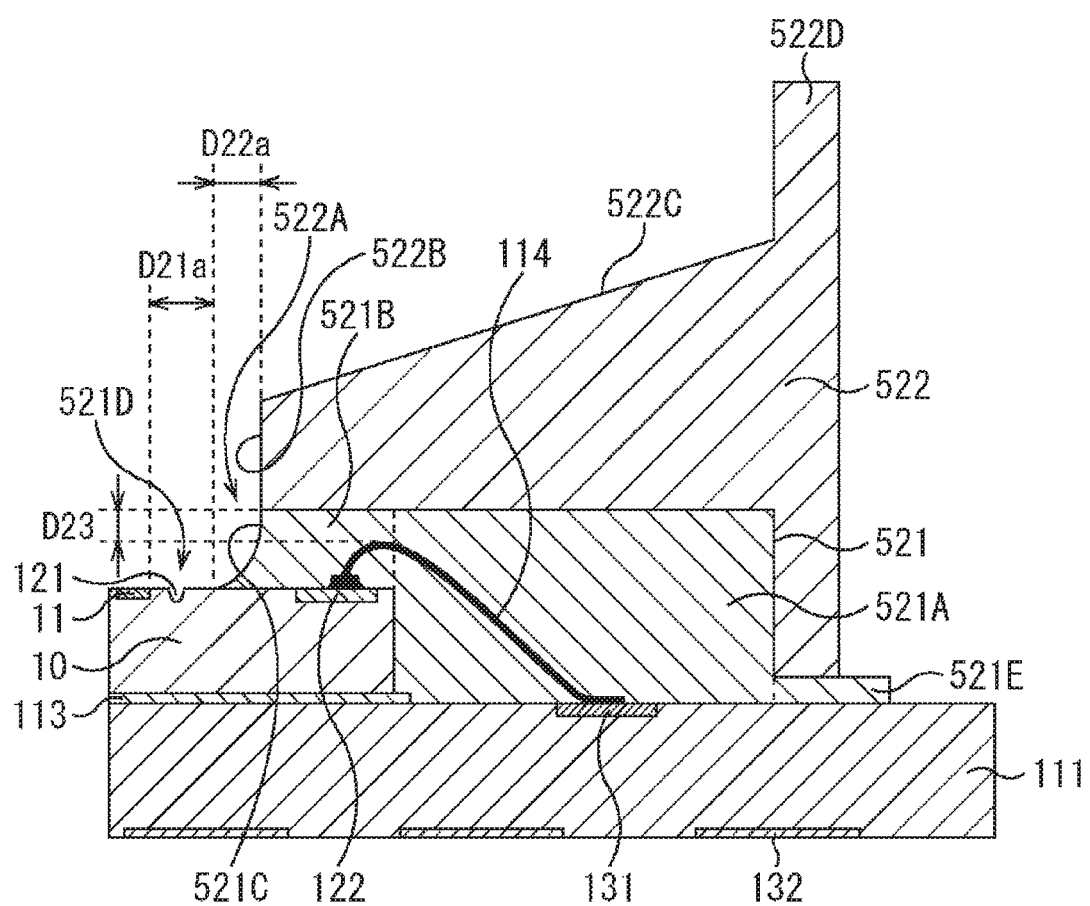
FIG. 18 is a schematic enlarged view of a section taken along line A-A' of FIG. 17.
Figure 19:
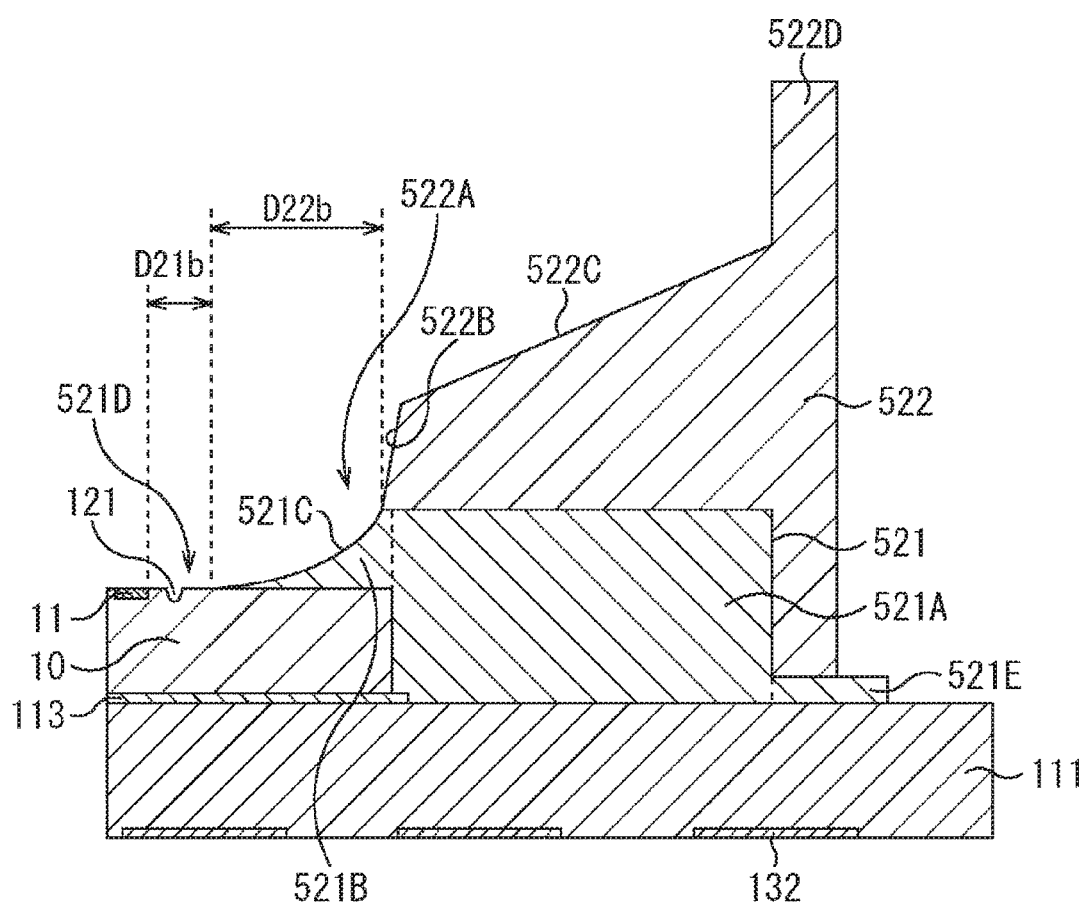
FIG. 19 is a schematic enlarged view of a section taken along line B-B' of FIG. 17.

FIG. 18 is a schematic enlarged view of a section taken along line A-A' near the center of a side of the electrode unit 11 of FIG. 17. FIG. 19 is a schematic enlarged view of a section taken along line B-B' near a corner of the electrode unit 11 of FIG. 17.

As described above with reference to FIG. 17, the opening 522A of the liquid-storage member 522 expands outward in the substantially arc shape near the four corners such that the space to the opening A of the sealing bonding portion 521 widens. Corresponding to this, the inclined face 521C of the sealing bonding portion 521 is more gradual in inclination and is longer on line B-B' than on line A-A'. That is, because the opening 522A expands outward in the substantially arc shape near the four corners, the area of the inclined face 521C, namely, the outward exposed area of the sealing bonding portion 521 widens near the four corners of the opening 521D of the sealing bonding portion 521.

This facilitates formation of the inner end of the sealing bonding portion 521. Specifically, at the time of bonding of the liquid-storage member 522 to the sealing bonding portion 521, bubbles occur easily near the four corners of the opening 521D of the sealing bonding portion 521.

Against this, the outward expansion of the opening 522A of the liquid-storage member 522 in the substantially arc shape near the four corners, inhibits bubbles from occurring near the four corners of the opening 521D of the sealing bonding portion 521 at the time of bonding of the liquid-storage member 522 to the sealing bonding portion 521. Furthermore, because the inclined face 521C is widely exposed outward near the four corners of the opening 521D of the sealing bonding portion 521, occurrence of bubbles on the inclined face 521C is easily detected. Moreover, the bubbles on the inclined face 521C can be removed easily by, for example, resin injection or the like. Therefore, the airtightness of the sealing bonding portion 521 improves, resulting in firmer protection of the electric connection between the cell potential detection chip 10 and the substrate 111. Furthermore, in a case where the amount of injection of resin varies due to production, the four corners of the electrode unit 11 is easily contaminated with the resin. However, the outward expansion in the substantially arc shape enables a margin in design against the resin contamination.

Note that, when the distance between the outer circumference of the electrode unit 11 and the inner circumference of the inclined face 521C (outer circumference of the opening 521D) on line A-A' is defined as $D21a$ and the distance between the outer circumference of the electrode unit 11 and the inner circumference of the inclined face 521C on line B-B' is defined as $D21b$, the distance $D21a$ and the distance $D21b$ are substantially equal. For example, the distance $21a$ and the distance $D21b$ are set to 100 μm or more in order to prevent a resin for forming the sealing bonding portion 521 from flowing into the electrode unit 11.

Furthermore, when the width of the inclined face 521C on line A-A' (distance between the inner circumference and the outer circumference of the inclined face 521C) is defined as $D22a$ and the width of the inclined face 521C on line B-B' is defined as $D22b$, the width $D22b$ is not less than the width $D22a$. For example, the width $D22a$ is set in the range from 100 μm to 500 μm, and the width $D22b$ is set to 500 μm or more.

Moreover, when the distance between the upper end of the sealing bonding portion 521 and the upper end of the wire 114 is defined as $D23$, for example, the distance $D23$ is set to 200 μm or more.

Note that, in the example of FIG. 19, the upper end of the inclined face 521C and the lower end of the face 522B on line B-B' are disposed inside the outer circumference of the cell potential detection chip 10, but may be disposed outside the outer circumference of the cell potential detection chip 10.

Here, an exemplary member combination of the sealing bonding portion 521 and the liquid-storage member 522 will be described.

For example, in a case where a member having a heat distortion temperature not more than the temperature at which the autoclave treatment is performed (hereinafter, referred to as the autoclave temperature) is used for the liquid-storage member 522, the liquid-storage member 522 is likely to deform due to the autoclave treatment. Against this, a member lower in post-cure elastic modulus than the liquid-storage member 522 is used for the sealing bonding portion 521, so that the sealing bonding portion 521 buffers the deformation of the liquid-storage member 522. As a result, even when the liquid-storage member 522 deforms due to the autoclave treatment, the liquid-storage member 522 is prevented from separating from the sealing bonding portion 521 or any gap is prevented from occurring therebetween. Thus, the culture solution is prevented from leaking from the liquid-storage portion.

For example, the autoclave treatment is performed in the environment at a temperature of 121° C., a relative humidity (RH) of 100%, and a pressure of 2 atmospheres. In this case, for the sealing bonding portion 521, for example, a harmless member including no ingredient harmful to the cell and having a post-cure elastic modulus of 1 MPa or less, a heat distortion temperature higher than the autoclave temperature (121° C.), and adhesion (adhesive ingredient), is used. For example, a silicone resin or the like having a post-cure elastic modulus of approximately 0.015 MPa, is used.

Meanwhile, for the liquid-storage member 522, a harmless member including no ingredient harmful to the cell and having a heat distortion temperature not more than the autoclave temperature (121° C.), can be used. For example, polyethylene (heat distortion temperature of approximately 60 to 80° C.), polypropylene (heat distortion temperature of approximately 95 to 100° C.), Teflon (registered trademark) (heat distortion temperature of approximately 121° C.), or the like can be used. Needless to say, for example, a Noryl resin having a heat distortion temperature higher than the autoclave temperature (heat distortion temperature of approximately 191° C.), or the like can be used for the liquid-storage member 522.

Furthermore, for example, a member having a heat distortion temperature higher than the autoclave temperature is used for the liquid-storage member 522, so that the liquid-storage member 522 can be prevented from deforming due to the autoclave treatment. For example, the Noryl resin (heat distortion temperature of approximately 191° C.) is used for the liquid-storage member 522, so that the liquid-storage member 522 can be inhibited from deforming due to the autoclave treatment. As a result, regardless of the elastic modulus of the sealing bonding portion 521, the liquid-storage member 522 is prevented from separating from the sealing bonding portion 521 or any gap is prevented from occurring therebetween. Thus, the culture solution is prevented from leaking from the liquid-storage portion.

Note that, because almost all organisms deaden due to boiling at 100° C., it can be considered that the autoclave temperature is set to 100° C. In this case, a harmless member including no ingredient harmful to the cell and having a heat distortion temperature higher than 100° C., can be used for the liquid-storage member 522. Instead of the Noryl resin described above, for example, Teflon (registered trademark) (heat distortion temperature of approximately 121° C.) or the like can be used.

Note that, in a case where a member having a heat distortion temperature higher than the autoclave temperature is use for the liquid-storage member 522, the post-cure elastic modulus of the sealing bonding portion 521 does not need considering. Therefore, regardless of post-cure elastic modulus, a harmless member including no ingredient harmful to the cell and having adhesion and a heat distortion temperature higher than the autoclave temperature, can be used for the sealing bonding portion 521. In addition to the silicone resin described above, for example, an epoxy resin having a post-cure elastic modulus of approximately 1734 MPa, or the like can be used.

<Method of Manufacturing Cell Potential Detection Device>

Figure 20:
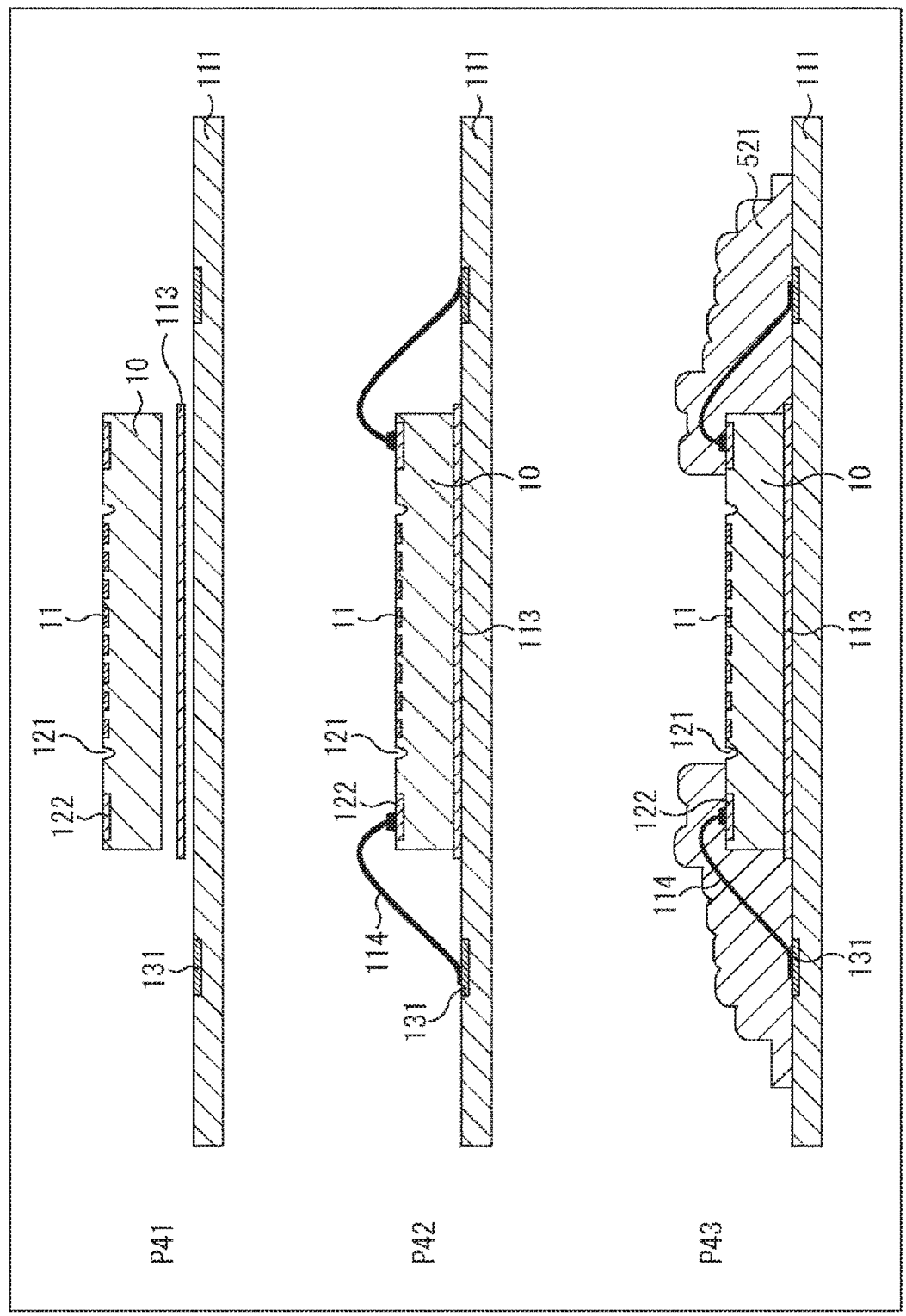
FIG. 20 explanatorily illustrates a method of manufacturing the cell potential detection device of FIG. 16.
Figure 21:
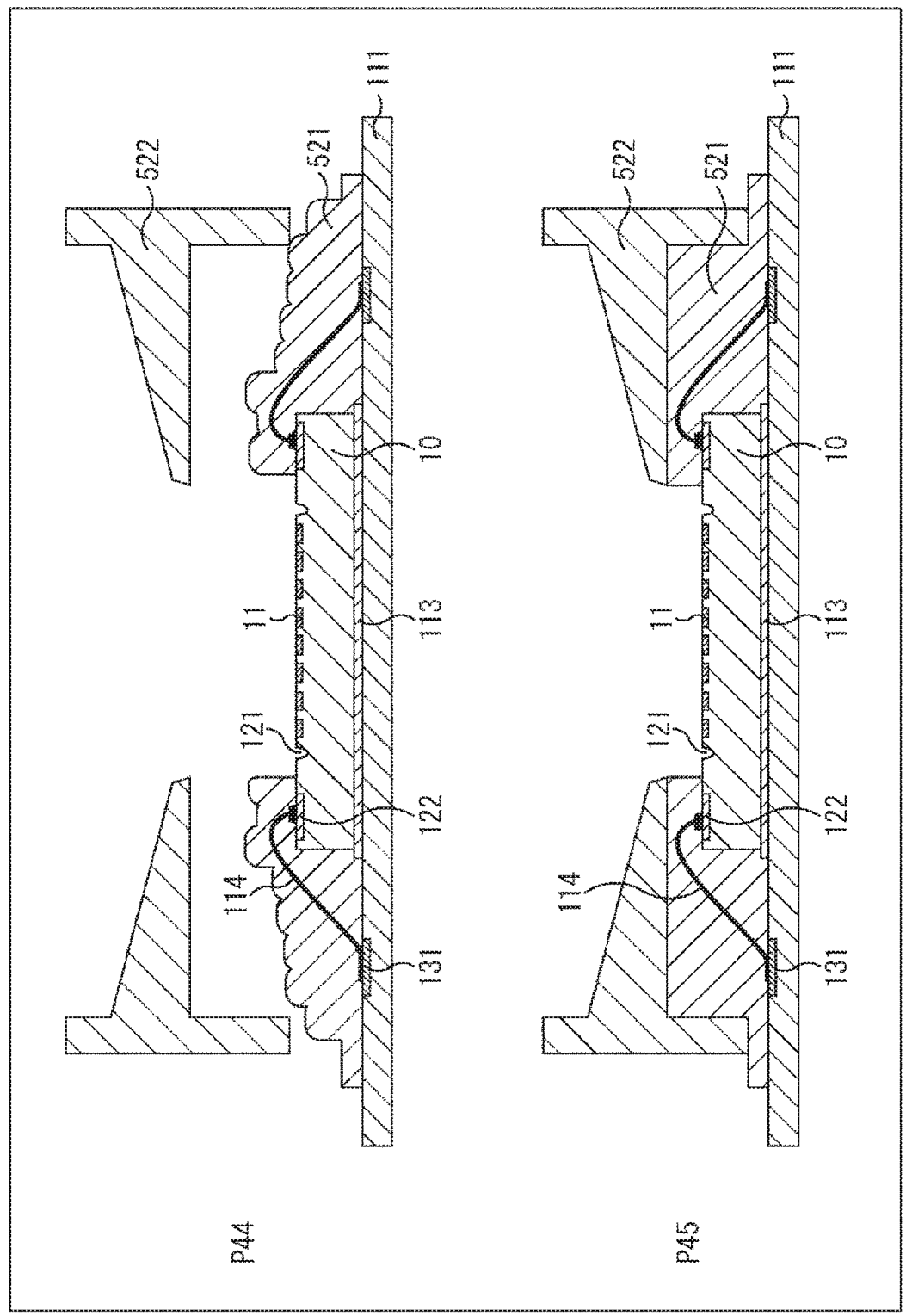
FIG. 21 explanatorily illustrates the method of manufacturing the cell potential detection device of FIG. 16.

Next, a method of manufacturing the cell potential detection device 501 will be described with reference to FIGS. 20 and 21. Note that, in the figures, parts unnecessary to the description are appropriately denoted with no reference sings. Furthermore, no external terminal 132 of the substrate 111 is illustrated.

Process P41 and process P42 are similar to process P1 and process P2 of FIG. 9, respectively, except for formation of no resist 251. That is the cell potential detection chip 10 is bonded to the component face of the substrate 111 and then the pads 122 of the cell potential detection chip 10 and the pads 131 of the substrate 111 are connected through the wires 114, respectively.

In process P43, the resin for forming the sealing bonding portion 521 is dispensed or potted. Therefore, the electric connection between the cell potential detection chip 10 and the substrate 111 is sealed by the sealing bonding portion 521.

In process P44, the liquid-storage member 522 is mounted onto the sealing bonding portion 521. That is the liquid-storage member 522 is bonded onto the sealing bonding portion 521. In this case, a molded product manufactured in advance by, for example, injection molding can be used for the liquid-storage member 522.

Note that, in this case, part of the resin for forming the sealing bonding portion 521 may be provided on the liquid-storage member 522 side.

In process P45, the sealing bonding portion 521 and the liquid-storage member 522 are cured by, for example, thermal curing or ultraviolet curing. Therefore, the sealing bonding portion 521 and the liquid-storage member 522 are secured to the substrate 111.

In the manner, the cell potential detection device 501 is manufactured.

Here, for the cell potential detection device 501, dispensing and potting the sealing bonding portion 521, mounting the liquid-storage member 522, which is the molded product, onto the sealing bonding portion 521, and curing the sealing bonding portion 521 and the liquid-storage member 522 result in formation of the liquid-storage sealing portion 511. Therefore, the productivity improves in comparison to the cell potential detection device 101 and the cell potential detection device 201 that need formation of the liquid-storage unit 112 by injection molding, and the cell potential detection device 301 and the cell potential detection device 401 that need bonding of the ring 321 and dispensing or potting of the liquid-storage sealing resin 322 in the ring 321.

7. Sixth Embodiment

Next, a seventh embodiment of the present technology will be described with reference to FIG. 22.

Figure 22:
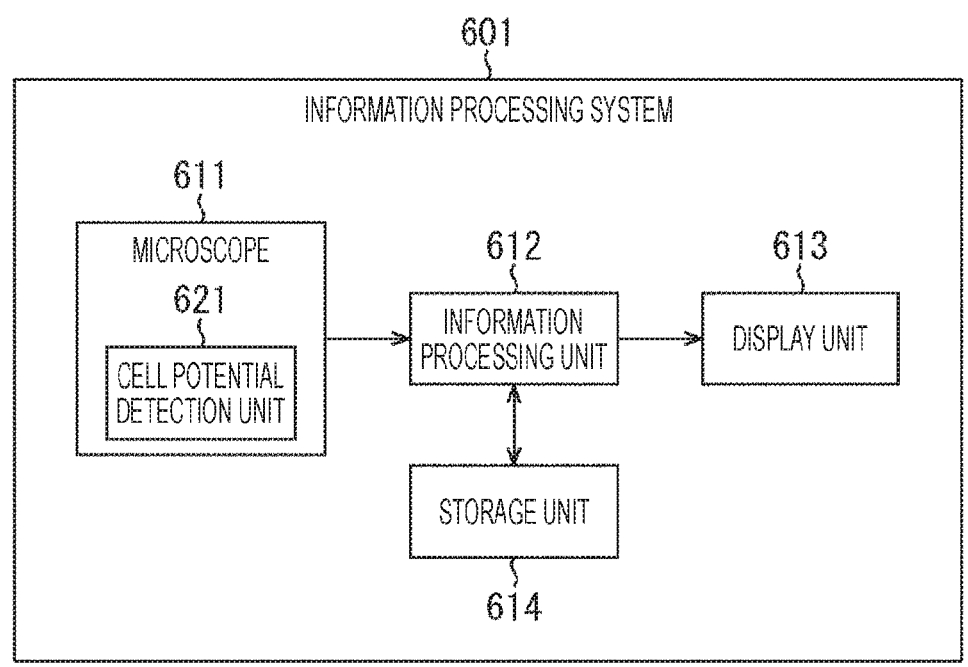
FIG. 22 is a block diagram of an exemplary configuration of an information processing system.

FIG. 22 is a block diagram of an exemplary configuration of an information processing system 601 according to the seventh embodiment of the present technology.

The information processing system 601 includes a microscope 611, an information processing unit 612, a display unit 613, and a storage unit 614.

The microscope 611 includes a cell potential detection unit 621. For the cell potential detection unit 621, for example, any of the cell potential detection devices 101 to 501*b* described above can be used. For example, the microscope 611 captures an image of a cell to be observed and supplies the acquired observation image to the information processing unit 612. Furthermore, the cell potential detection unit 621 detects the action potential of the cell to be observed and supplies a detection signal indicating a result of the detection, to the information processing unit 612.

The information processing unit 612 includes, for example, a computer, a processor, or the like. The information processing unit 612 performs, for example, various types of processing to the observation image and the detection signal, generates data indicating an observation result of the cell, and causes the display unit 613 to display the data or the storage unit 614 to store the data.

The display unit 613 includes, for example, various types of displays.

The storage unit 614 includes, for example, various types of memories.

Note that the processing of the information processing unit 612 can be performed by hardware or by software. In a case where a series of processing is performed by software, a program included in the software is installed onto, for example, the computer included in the information processing unit 612. Here, examples of the computer include a computer built in dedicated hardware, a general-purpose personal computer capable of performing various types of functions due to installation of various types of programs, and the like.

Note that the program to be executed by the computer may be a program for performing processing on a time series basis or a program for performing processing in parallel or with necessary timing at which a call is made, for example.

Furthermore, the program to be executed by the computer can be recorded in, for example, a removable medium serving as a packaged medium or the like (e.g., storage unit 614), for provision. Furthermore, the program can be provided through a wired transfer medium or a wireless transfer medium, such as a local area network, the Internet, or digital satellite broadcasting.

8. Modifications

Modifications of the embodiments of the present technology described above will be described below.

For example, a member having a heat distortion temperature higher than the autoclave temperature, may be used for the liquid-storage unit 112 of the cell potential detection device 101 or the cell potential detection device 201. Therefore, the liquid-storage unit 112 is prevented from separating from the substrate 111 or any gap is prevented from occurring therebetween, due to the autoclave treatment. Thus, the culture solution is prevented from leaking from the liquid-storage portion.

Furthermore, for example, a member having a heat distortion temperature higher than the autoclave temperature, may be used for the liquid-storage sealing resin 322 of the cell potential detection device 301 or the cell potential detection device 401. Therefore, the liquid-storage sealing resin 322 is prevented from separating from the substrate 111 or any gap is prevented from occurring therebetween, due to the autoclave treatment. Thus, the culture solution is prevented from leaking from the liquid-storage portion.

9. Others

The system in the present specification means an aggregate of a plurality of constituent elements (e.g., devices and modules (components)), regardless of whether or not all the constituent elements are located in the same housing. Therefore, a plurality of devices connected through a network, the devices each being housed in a different housing, and one device including a plurality of modules housed in one housing, are involved all in the system.

Furthermore, embodiments of the present technology are not limited to the embodiments described above, and thus various alterations can be made without departing from the scope of the spirit of the present technology.

For example, the present technology can have a configuration of cloud computing in which a plurality of devices dividedly processes one function in cooperation through a network.

<Exemplary Combinations of Configurations>

The present technology can have the following configurations.

(1)

A cell potential detection device including:

a cell potential detection chip including an electrode unit that detects potential of a cell;

a substrate on which the cell potential detection chip is implemented;

a first member sealing a connection electrically connecting the cell potential detection chip and the substrate; and a second member layered on the first member, the second member forming a liquid-storage portion that stores culture solution for the cell, together with the first member.

(2)

The cell potential detection device according to (1) above, in which a post-cure elastic modulus of the first member is lower than a post-cure elastic modulus of the second member.

(3)

The cell potential detection device according to (2) above, in which the post-cure elastic modulus of the first member is 1 MPa or less.

(4)

The cell potential detection device according to (3) above, in which the first member includes silicone resin.

(5)

The cell potential detection device according to (2) or (3) above, in which the second member includes polyethylene, Noryl resin, Teflon (registered trademark), or polypropylene.

(6)

The cell potential detection device according to any of (1) to (3) above, in which a heat distortion temperature of the second member is higher than a temperature at which the cell potential detection device is subjected to autoclave treatment.

(7)

The cell potential detection device according to (6) above, in which the heat distortion temperature of the second member is higher than 100° C.

(8)

The cell potential detection device according to (7) above, in which the second member includes Noryl resin or Teflon (registered trademark).

(9)

The cell potential detection device according to (6) above, in which the first member includes silicone resin or epoxy resin.

(10)

The cell potential detection device according to any of (1) to (9) above, in which the first member has adhesion.

(11)

The cell potential detection device according to any of (1) to (10) above, in which the first member has:

a first opening ranging over a periphery of the electrode unit; and a first face surrounding a periphery of the first opening, and the second member has:

a second opening ranging over the periphery of the first opening; and a second face surrounding a periphery of the second opening.

(12)

The cell potential detection device according to (11) above, in which the first opening is substantially rectangular, and the second opening has space expanding to the first opening near four corners of the first opening.

(13)

The cell potential detection device according to (11) or (12) above, in which the liquid-storage portion includes:

an exposed portion exposed through the first opening of a face of the cell potential detection chip, the electrode unit being disposed on the face;

the first face; and the second face.

(14)

The cell potential detection device according to any of (11) to (13) above, in which the second member further includes a wall surrounding an outer circumference of the second face.

(15)

The cell potential detection device according to any of (1) to (14) above, in which the connection includes:

a first pad disposed on a periphery of the electrode unit on the cell potential detection chip;

a second pad disposed on a periphery of the cell potential detection chip on the substrate; and a wire connecting the first pad and the second pad.

(16)

A method of manufacturing a cell potential detection device, the method including:

a first process of sealing, with a first member, a connection electrically connecting a cell potential detection chip including an electrode unit that detects potential of a cell and a substrate on which the cell potential detection chip is implemented; and a second process of layering a second member on the first member such that the second member forms a liquid-storage portion that stores culture solution for the cell, together with the first member.

(17)

An information processing system including:

a cell potential detection unit configured to detect potential of a cell; and an information processing unit configured to process a detection signal of the potential of the cell, in which the cell potential detection unit includes:

a cell potential detection chip including an electrode unit that detects the potential of the cell, the cell potential detection chip being configured to output the detection signal;

a substrate on which the cell potential detection chip is implemented;

a first member sealing a connection electrically connecting the cell potential detection chip and the substrate; and a second member layered on the first member, the second member forming a liquid-storage portion that stores culture solution for the cell, together with the first member.

Note that the effects in the present specification are just exemplary and are not limitative, and thus other effects may be provided.

REFERENCE SIGNS LIST

10 Cell potential detection chip
11 Electrode unit
101 Cell potential detection device
111 Substrate
112 Liquid-storage unit
112A Opening
112B Inclined face
112C Inclined face
112D Wall
114 Wire
122 Pad
131 Pad
201 Cell potential detection chip
211 Overcoat
301 Cell potential detection device
311 Liquid-storage sealing portion
321 Ring
322 Liquid-storage sealing resin
322A Opening
322B Inclined face
401 Cell potential detection device
411 Overcoat
501, 501a, 501b Cell potential detection device
511 Liquid-storage sealing portion
521 Sealing bonding portion
521C Inclined face
521D Opening
522 Liquid-storage member
522A Opening
522B Face
522C Inclined face
522D Wall
601 Information processing system
611 Microscope
612 Information processing unit
613 Display unit
621 Cell potential detection unit

The invention claimed is:

1. A cell potential detection device, comprising:

a substrate;

a cell potential detection chip on the substrate, wherein the cell potential detection chip includes an electrode unit configured to detect potential of a cell;

a connection configured to electrically connect the cell potential detection chip and the substrate;

a first member that seals the connection, wherein
the first member includes a first opening that ranges over a periphery of the electrode unit, and
the first opening is substantially rectangular; and
a second member on the first member, wherein
the second member corresponds to a liquid-storage portion, wherein the liquid-storage portion is configured to store a culture solution for the cell, together with the first member,
the second member includes a second opening that ranges over a periphery of the first opening, and
the second opening includes space that expands near four corners of the first opening.

2. The cell potential detection device according to claim 1, wherein a post-cure elastic modulus of the first member is lower than a post-cure elastic modulus of the second member.

3. The cell potential detection device according to claim 2, wherein the post-cure elastic modulus of the first member is 1 MPa or less.

4. The cell potential detection device according to claim 3, wherein the first member includes silicone resin.

5. The cell potential detection device according to claim 2, wherein the second member includes polyethylene, Noryl resin, Teflon (registered trademark), or polypropylene.

6. The cell potential detection device according to claim 1, wherein a heat distortion temperature of the second member is higher than an autoclave treatment temperature of the cell potential detection device.

7. The cell potential detection device according to claim 6, wherein the heat distortion temperature of the second member is higher than 100° C.

8. The cell potential detection device according to claim 7, wherein the second member includes Noryl resin or Teflon (registered trademark).

9. The cell potential detection device according to claim 6, wherein the first member includes silicone resin or epoxy resin.

10. The cell potential detection device according to claim 1, wherein the first member includes an adhesive ingredient.

11. The cell potential detection device according to claim 1, wherein
the first member includes
a first face that surrounds the periphery of the first opening, and the second member includes
a second face that surrounds a periphery of the second opening.

12. The cell potential detection device according to claim 11, wherein
the liquid-storage portion includes:
an exposed portion of a face of the cell potential detection chip, wherein
the first opening exposes the exposed portion, and
the electrode unit is on the face of the cell potential detection chip;
the first face; and
the second face.

13. The cell potential detection device according to claim 11, wherein the second member further includes a wall that surrounds an outer circumference of the second face.

14. The cell potential detection device according to claim 1, wherein the connection includes:
a first pad on the periphery of the electrode unit;
a second pad on the substrate, wherein the second pad surrounds a periphery of the cell potential detection chip; and
a wire that connects the first pad and the second pad.

15. A method of manufacturing a cell potential detection device, the method comprising:
sealing, with a first member, a connection electrically connecting a cell potential detection chip and a substrate, wherein
the cell potential detection chip is on the substrate, and
the cell potential detection chip includes an electrode unit configured to detect potential of a cell; and
layering a second member on the first member, wherein
the second member corresponds to a liquid-storage portion, and
the liquid-storage portion is configured to store a culture solution for the cell, together with the first member.

16. An information processing system, comprising:
a cell potential detection unit configured to detect potential of a cell; and
an information processing unit configured to process a detection signal of the potential of the cell, wherein
the cell potential detection unit includes:
a substrate;
a cell potential detection chip on the substrate, wherein
the cell potential detection chip includes an electrode unit configured to detect the potential of the cell, and
the cell potential detection chip is configured to output the detection signal;
a connection configured to electrically connect the cell potential detection chip and the substrate;
a first member that seals the connection, wherein
the first member includes a first opening that ranges over a periphery of the electrode unit, and
the first opening is substantially rectangular; and
a second member on the first member, wherein
the second member corresponds to a liquid-storage portion,
the liquid-storage portion is configured to store a culture solution for the cell, together with the first member,
the second member includes a second opening that ranges over a periphery of the first opening, and
the second opening includes space that expands near four corners of the first opening.

17. A cell potential detection device, comprising:
a substrate;
a cell potential detection chip on the substrate, wherein
the cell potential detection chip includes an electrode unit configured to detect potential of a cell;
a connection configured to electrically connect the cell potential detection chip and the substrate;
a first member that seals the connection, wherein the first member includes a first opening that ranges over a periphery of the electrode unit; and
a second member on the first member, wherein
the second member corresponds to a liquid-storage portion,
the liquid-storage portion is configured to store a culture solution for the cell, together with the first member,
the second member includes a second opening that ranges over a periphery of the first opening, and
the liquid-storage portion includes:
an exposed portion of a face of the cell potential detection chip, wherein the first opening exposes the exposed portion,
the electrode unit is on the face of the cell potential detection chip, a first face that surrounds the periphery of the first opening, and a second face that surrounds a periphery of the second opening.

* * * * *